(12) United States Patent
Vitalis et al.

(10) Patent No.: US 9,932,565 B2
(45) Date of Patent: Apr. 3, 2018

(54) DEPHOSPHORYLATED LYSOSOMAL STORAGE DISEASE PROTEINS AND METHODS OF USE THEREOF

(71) Applicant: biOasis Technologies, Inc., Vancouver (CA)

(72) Inventors: Timothy Z. Vitalis, Vancouver (CA); Reinhard Gabathuler, Montreal (CA)

(73) Assignee: biOasis Technologies, Inc., Vancouver (CA)

( * ) Notice: Subject to any disclaimer, the term of this patent is extended or adjusted under 35 U.S.C. 154(b) by 0 days.

(21) Appl. No.: 13/955,794

(22) Filed: Jul. 31, 2013

(65) Prior Publication Data

US 2014/0178350 A1  Jun. 26, 2014

Related U.S. Application Data

(60) Provisional application No. 61/677,959, filed on Jul. 31, 2012.

(51) Int. Cl.
| | | |
|---|---|---|
| *C12N 9/16* | (2006.01) | |
| *C12N 11/00* | (2006.01) | |
| *A61K 38/00* | (2006.01) | |
| *A61K 47/48* | (2006.01) | |

(52) U.S. Cl.
CPC .............. *C12N 9/16* (2013.01); *A61K 47/483* (2013.01); *C12N 11/00* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,866,042 A | 9/1989 | Neuwelt | |
| 5,186,941 A | 2/1993 | Callahan et al. | |
| 5,672,683 A | 9/1997 | Friden et al. | |
| 5,798,239 A | 8/1998 | Wilson et al. | |
| 5,932,211 A | 8/1999 | Wilson et al. | |
| 5,981,194 A | 11/1999 | Jefferies et al. | |
| 6,261,595 B1 | 7/2001 | Stanley et al. | |
| 6,455,494 B1 | 9/2002 | Jefferies et al. | |
| 6,537,785 B1* | 3/2003 | Canfield ................ | C07K 16/40 424/94.1 |
| 6,596,541 B2 | 7/2003 | Murphy et al. | |
| 7,138,371 B2 | 11/2006 | DeFrees et al. | |
| 7,179,617 B2 | 2/2007 | DeFrees et al. | |
| 7,700,554 B2 | 4/2010 | Beliveau et al. | |
| 8,546,319 B2 | 10/2013 | Starr et al. | |
| 8,722,019 B2 | 5/2014 | Jeffries et al. | |
| 9,150,846 B2 | 10/2015 | Hutchison et al. | |
| 9,161,992 B2 | 10/2015 | Jefferies et al. | |
| 9,364,567 B2 | 6/2016 | Vitalis et al. | |
| 2002/0059032 A1 | 5/2002 | Ferrer et al. | |
| 2002/0119095 A1 | 8/2002 | Gabathuler et al. | |
| 2003/0072761 A1 | 4/2003 | LeBowitz | |
| 2003/0129186 A1 | 7/2003 | Beliveau et al. | |
| 2004/0055022 A1 | 3/2004 | Cheng et al. | |
| 2004/0137557 A1 | 7/2004 | DeFrees et al. | |
| 2005/0026823 A1 | 2/2005 | Zankel et al. | |
| 2005/0158296 A1 | 7/2005 | Starr et al. | |
| 2007/0167365 A1 | 7/2007 | Beliveau et al. | |
| 2008/0014188 A1 | 1/2008 | Zankel et al. | |
| 2008/0152645 A1 | 6/2008 | Pardridge et al. | |
| 2009/0226421 A1 | 9/2009 | Parren et al. | |
| 2010/0129359 A1 | 5/2010 | Tobinick | |
| 2010/0183581 A1 | 7/2010 | Beliveau et al. | |
| 2010/0297120 A1 | 11/2010 | Beliveau et al. | |
| 2010/0303797 A1 | 12/2010 | Starr et al. | |
| 2011/0093962 A1 | 4/2011 | Heidbrink et al. | |
| 2011/0142763 A1 | 6/2011 | Zankel et al. | |
| 2011/0318323 A1* | 12/2011 | Zhu ..................... | A61K 9/0085 424/94.3 |
| 2012/0003202 A1* | 1/2012 | Calias .................. | A61K 9/0085 424/94.3 |
| 2012/0107302 A1 | 5/2012 | Berry et al. | |
| 2013/0108548 A1 | 5/2013 | Vlieghe et al. | |
| 2013/0183368 A1 | 7/2013 | Hutchison et al. | |
| 2013/0236442 A1 | 9/2013 | Lee et al. | |
| 2014/0105880 A1 | 4/2014 | Starr et al. | |
| 2014/0322132 A1 | 10/2014 | Vitalis et al. | |
| 2015/0056218 A1 | 2/2015 | Jefferies et al. | |
| 2015/0093399 A1 | 4/2015 | Jefferies | |
| 2016/0053237 A1 | 2/2016 | Jefferies et al. | |
| 2016/0324937 A1 | 11/2016 | Vitalis et al. | |
| 2016/0347821 A1 | 12/2016 | Vitalis et al. | |
| 2017/0049897 A1 | 2/2017 | Jefferies et al. | |
| 2017/0204386 A1 | 7/2017 | Vitalis et al. | |

FOREIGN PATENT DOCUMENTS

| | | |
|---|---|---|
| GB | 2188637 | 10/1987 |
| WO | WO 89/04663 | 6/1989 |
| WO | WO 93/11161 | 6/1993 |
| WO | WO 94/01463 | 1/1994 |
| WO | WO 98/23646 | 6/1998 |
| WO | WO 2000/050636 | 8/2000 |
| WO | WO 2001/059459 | 8/2001 |
| WO | WO 2001/083722 | 8/2001 |
| WO | WO 2002/013843 | 2/2002 |
| WO | WO 2002/013873 | 2/2002 |

(Continued)

OTHER PUBLICATIONS

Bielicki et al., Human liver iduronate-2-sulfatase, Biochem. J. (271):75-86, 1990.*

(Continued)

*Primary Examiner* — Taeyoon Kim
*Assistant Examiner* — Srikanth Patury

(57) ABSTRACT

Provided are substantially dephosphorylated forms of lysosomal storage disease (LSD) proteins, including dephosphorylated forms of iduronate-2-sulfatase (IDS, or I2D) and iduronidase (IDU), having increased ability to traverse or penetrate the blood brain barrier (BBB) relative to phosphorylated forms of the protein, and p97 conjugates thereof. Also provided are compositions comprising such dephosphorylated LSD proteins and p97 conjugates, and methods of use thereof, for instance, to treat any one or more lysosomal storage diseases, such as Hunter Syndrome (or MPS Type II).

7 Claims, 6 Drawing Sheets

(56) References Cited

FOREIGN PATENT DOCUMENTS

| WO | WO 2003/009815 | 2/2003 |
|---|---|---|
| WO | WO 2003/057179 | 7/2003 |
| WO | WO 2004/078215 | 9/2004 |
| WO | WO 2005/034979 | 4/2005 |
| WO | WO 2006/079372 | 8/2006 |
| WO | WO 2008/022349 | 2/2008 |
| WO | WO 2008/118013 | 10/2008 |
| WO | WO 2009/019314 | 2/2009 |
| WO | WO 2011/044542 | 4/2011 |
| WO | WO 2011/131693 | 10/2011 |
| WO | WO 2011/163649 | 12/2011 |
| WO | WO 2013/006706 | 1/2013 |
| WO | WO 2013/022738 | 2/2013 |
| WO | WO 2014/005036 | 1/2014 |
| WO | WO 2014/022515 | 2/2014 |
| WO | WO 2014/064258 | 5/2014 |
| WO | WO 2014/128504 | 8/2014 |
| WO | WO 2014/160438 | 10/2014 |
| WO | WO 2015/031673 | 3/2015 |
| WO | WO 2015/117121 | 8/2015 |
| WO | WO 2015/126729 | 8/2015 |
| WO | WO 2015/168521 | 11/2015 |

OTHER PUBLICATIONS

Braulke et al., Sorting of lysosomal proteins, Biochimica et Biophysica Acta, 1793, 605-614, 2009.*
Kakkis'PEP, Overexpression of the Human Lysosomal Enzyme alpha-L-iduronidase in CHO cells, Protein Expression and Purification, vol. 5, Iss. 3, Jun. 1994, pp. 225-232.*
Froissart et al., Processing of iduronate 2-sulphatase in human fibroblasts, Biochem. J., 309, 425-430, 1995.*
Supplementary European Search Report for European Application No. 03717870.4, dated Oct. 2, 2007, 4 pages.
Office Action in U.S. Appl. No. 10/501,028 dated Dec. 23, 2009, 8 pages.
Office Action in U.S. Appl. No. 10/501,028 dated Aug. 17, 2009, 8 pages.
Office Action in U.S. Appl. No. 10/501,028 dated Oct. 29, 2008, 11 pages.
Office Action in U.S. Appl. No. 10/501,028 dated Jul. 31, 2008, 9 pages.
Office Action in U.S. Appl. No. 10/501,028 dated Jan. 29, 2008, 8 pages.
International Search Report for International Application No. PCT/US2003/000894, dated Sep. 10, 2003, 3 pages.
International Preliminary Examination Report for International Application No. PCT/US2003/000894, dated Feb. 14, 2005, 5 pages.
Supplementary European Search Report for European Application No. 11178022.7, dated Nov. 25, 2011, 6 pages.
Office Action for U.S. Appl. No. 12/729,792, dated Jun. 12, 2013, 9 pages.
Office Action for U.S. Appl. No. 12/729,792, dated Aug. 20, 2012, 9 pages.
Office Action for U.S. Appl. No. 12/729,792, dated Jan. 11, 2013, 11 pages.
Office Action for U.S. Appl. No. 13/969,280, dated Sep. 22, 2014, 5 pages.
Office Action for U.S. Appl. No. 13/969,280, dated Mar. 4, 2015, 10 pages.
International Search Report and Written Opinion for International Application No. PCT/US2014/026620, dated Sep. 17, 2014, 15 pages.
Examination Report for Australian Application No. 2012278944, dated Aug. 26, 2014, 3 pages.
Office Action for U.S. Appl. No. 13/542,435, dated Dec. 3, 2014, 27 pages.
International Preliminary Report on Patentability for International Application No. PCT/US2012/045568, dated Jan. 7, 2014, 5 pages.
International Search Report and Written Opinion for International Application No. PCT/US2012/045568, dated Sep. 27, 2012, 9 pages.
Examination Report for Australian Application No. 2012294673, dated Sep. 16, 2014, 4 pages.
Notice of Allowance in U.S. Appl. No. 13/566,260, dated Dec. 26, 2013, 8 pages.
Office Action in U.S. Appl. No. 13/566,260, dated Sep. 5, 2013, 6 pages.
International Preliminary Report on Patentability for International Application No. PCT/US2012/049475, dated Feb. 11, 2014, 7 pages.
International Search Report and Written Opinion for International Application No. PCT/US2012/049475, dated Oct. 25, 2012, 9 pages.
International Search Report and Written Opinion for International Application No. PCT/US2013/052939, dated Oct. 31, 2013, 14 pages.
International Preliminary Report on Patentability for International Application No. PCT/US2013/052939, dated Feb. 3, 2015, 9 pages.
Invitation to Pay Additional Fees and Partial International Search for International Application No. PCT/US2014/053257, dated Jan. 12, 2015, 10 pages.
Aktas, Y. et al., "Development and brain delivery of chitosan-PEG nanoparticles functionalized with the monoclonal antibody OX26," Bioconjugate Chem,16(6):1503-1511 (2005).
Asano, N. et al., "In vitro inhibition and intracellular enhancement of lysosomal α-galactosidase A activity in Fabry lymphoblasts by 1-deoxygalactonojirimycin and its derivatives," Eur. J. Biochem., 267(13):4179-4186 (2000).
Begley, D. J. et al., "Lysosomal storage diseases and the blood-brain barrier," Current Pharmaceutical Design, 14(16):1566-1580 (2008).
Bickel, U. et al., "Pharmacologic effects in vivo in brain by vector-mediated peptide drug delivery," Proc. Natl. Acad. Sci. USA, 90(7):2618-2622 (1993).
Bickel, U. et al., "In vivo demonstration of subcellular localization of anti-transferrin receptor monoclonal antibody-colloidal gold conjugate in brain capillary endothelium," Journal of Histochemistry and Cytochemistry, 42(11):1493-1497 (1994).
Bickel, U. et al., "In vivo cleavability of a disulfide-based chimeric opioid peptide in rat brain," Bioconjugate Chem, 6(2):211-218 (1995).
Bickel, U. et al., "Delivery of peptides and proteins through the blood-brain barrier," Advanced Drug Delivery Review, 46(1-3):247-279 (2001).
Bielicki, J. et al., "Recombinant human iduronate-2-sulphatase: correction of mucopolysaccharidosis-type II fibroblasts and characterization of the purified enzyme," Biochemical Journal, 289(Pt. 1):241-246 (1993).
Blattler, W. A. et al., "New heterobifunctional protein cross-linking reagent that forms an acid-labile link," Biochem., 24:1517-1524 (1985).
Boado, R. J. et al., "Cloning and expression in Pichia pastoris of a genetically engineered single chain antibody against the rat transferrin receptor," Journal of Drug Targeting, 8(6):403-412 (2000).
Broadwell, R. D. et al., "Transcytosis of protein through the mammalian cerebral epithelium and endothelium. III. Receptor-mediated transcytosis through the blood-brain barrier of blood-borne transferrin and antibody against the transferrin receptor," Experimental Neurology, 142(1):47-65 (1996).
Cerletti, A. et al., "Endocytosis and transcytosis of an immunoliposome-based brain drug delivery system," Journal of Drug Targeting, 8(6):435-446 (2000).
Chakraborty, C. et al., "Future prospects of nanoparticles on brain targeted drug delivery," Journal of Neuro-Oncology, 93(2):285-286 (2008).
Chen, Q. et al., "Efficient Synthesis of Doxorubicin Melanotransferrin p97 Conjugates Through SMCC Linker," Synthetic Communications, 34(13) (2004).

(56) References Cited

OTHER PUBLICATIONS

Chen, C.-H. B. et al., "Aptamer-based endocytosis of a lysosomal enzyme," Proceedings of the National Academy of Sciences, 105(41):15908-15913 (2008).
Daniele, A. et al., "Uptake of recombinant iduronate-2-sulfatase into neuronal and glial cells in vitro," Biochimica et Biophysica Acta., 1588(3):203-209 (2002).
Deguchi, Y. et al., "Retention of biologic activity of human epidermal growth factor following conjugation to a blood-brain barrier drug delivery vector via an extended poly (ethylene glycol) linker," Bioconjugate Chem., 10(1):32-37 (1999).
Delabarre, B. et al., "Central Pore Residues Mediate the p97/VCP activity required for ERAD," Molecular Cell, 19(22):451-462 (2006).
Demeule, M. et al., "High transcytosis of melanotransferrin (P97) across the blood-brain barrier," Journal of Neurochemistry, 83:924-933 (2002).
Demeule, M. et al., "Regulation of plasminogen activation: A role for melantransferrin (p97) in cell migration," Blood, 102(5):1723-1731 (2003).
Dorr, R. T. et al., "In vitro rat myocyte cardiotoxicity model for antitumor antibiotics using adenosine triphosphate/protein ratios," Cancer Research, 48:5222-5227 (1988).
Endo, N. et al., "In-Vitro Cytotoxicity of a Human Serum Albumin-mediated Conjugate of Methotrexate with Anti-MM46 Monoclonal Antibody," Cancer Research, 47(4):1076-1080 (1987).
Enzyme: L-iduronidase. EC 3.2.1.76. http://www.chem.qmul.ac.uk/iubmb/enzyme/EC3/2/1/76.html, 2 pages (Printed Feb. 17, 2009).
Enzyme: N-acetylglucosaminidase. EC 3.2.1.96. http://www.chem.qmul.ac.uk/iubmb/enzyme/EC3/2/1/96.html, 2 pages (Printed Feb. 17, 2009).
Enzyme: β-N-acetylhexosaminidase. EC 3.2.1.52. http://www.chem.qmul.ac.uk/iubmb/enzyme/EC3/2/1/52.html, 2 pages (Printed Dec. 17, 2009).
Friden, P. M., "Anti-transferrin receptor antibody and antibody-drug conjugates cross the blood-brain barrier," Proc. Natl. Acad. Sci. USA, 88(11):4771-4775 (1991).
Gabathuler, R. et al., "Incorporation of transcend (melanotransferrin or MTf) in a therapeutic antibody allows its transport across the blood-brain barrier for the treatment of brain disorders," Society for Neuroscience Abstract Viewer and Itinerary Planner, vol. 42 (2012), XP8173954, & 42nd Annual Meeting of the Society for.
Geuze, H. J. et al., "Possible Pathways for Lysosomal Enzyme Delivery," Journal of Cell Biology, 101:2253-2262 (1985).
Gosk, S. et al., "Targeting anti-transferrin receptor antibody (OX26) and OX26-conjugated liposomes to brain capillary endothelial cells using in situ perfusion," Journal of Cerebral Blood Flow & Metabolism, 24(11):1193-1204 (2004).
Grubb, J. H. et al., "Chemically modified β-glucuronidase crosses blood-brain barrier and clears neuronal storage in murine mucopolysaccharidosis VII," Proceedings of the National Academy of Sciences, 105(7):2616-2621 (2008).
Huwyler, J. et al., "Receptor mediated delivery of daunomycin using immunoliposomes: pharmacokinetics and tissue distribution in the rat," Journal of Phamacology & Experimental Therapeutics, 282(3):1541-1546 (1997).
Jefferies, W. A. et al., "Transferrin receptor on endothelium of brain capillaries," Nature, 312:162-163 (1984).
Jefferies, W. A. et al., "Analysis of lymphopoletic stem cells with a monoclonal antibody to the rat transferrin receptor," Immunology, 54(2):333-341 (1985).
Jolly, R. D. et al., "Lysosomal storage diseases of animals: an essay in comparative pathology," Veterinary Pathology Online, 34:527-548 (1997).
Kakkis, E. et al., "Successful induction of immune tolerance to enzyme replacement therapy in canine mucopolysaccharidosis I," Proceedings of the National Academy of Sciences, 101(3):829-834 (2004).
Kang, Y. S. et al., "Pharmacokinetics and organ clearance of a 3'-biotinylated, internaly [32P]-labeled phosphodiester oligodeoxynucleotide coupled to a neutral avidin/monoclonal antibody conjugate," Drug Metabolism and Disposition, 23(1):55-59 (1995).
Kang, Y. S. et al., "Stability of the disulfide bond in an avidin-biotin linked chimeric peptide during in vivo transcytosis through brain endothelial cells," Journal of Drug Targeting, 8(6):425-434 (2000).
Kang, Y. S. et al., "Use of neutral avidin improves pharmacokinetics and brain delivery of biotin bound to an avidin-monoclonal antibody conjugate," Journal of Pharmacology & Experimental Therapeutics, 269(1):344-350 (1994).
Karkan, D. et al., "A unique carrier for delivery of therapeutic compounds beyond the blood-brain barrier," PLOS One, 3(6):E2469.1-E2469.14 (2008).
King, T. P. et al., "Preparation of protein conjugates via intermolecular hydrazone linkage," Biochem, 25:5774-5779 (1986).
Kurihara, A. et al., "Aβ1-40 Peptide radiopharmaceuticals for brain amyloid imaing: III-Inchelation, conjugation to poly(ethylene glycol)-biotin linkers, and autoradiography with Alzheimer's disease brain sections," Bioconjugate Chem, 11:380-386 (2000).
Mahapatro, A. et al., "Biodegradable nanoparticles are excellent vehicle for site directed in-vivo delivery of drugs and vaccines," Journal of Nanobiotechnology, 9(1):55 (2011).
Moos, T. et al., "Restricted transport of anti-transferrin receptor antibody (OX26) through the blood-brain barrier in the rat," Journal of Neurochemistry, 79(1):119-129 (2001).
Moroo, I. et al., "Identification of a novel route of iron transcytosis across the mammalian blood-brain barrier," Microcirculation, 10(6):457-462 (2003).
Muraszoko, K. et al., "Pharmacokinetics and toxicology of immunotoxins administered into the subarachnoid space in nonhuman primates and rodents," Cancer Research, 53(16):3752-3757 (1993).
Muruganandam, A. et al., "Selection of phage-displayed llama single-domain antibodies that transmigrate across human blood-brain barrier endothelium," FASEB Journal, 16(2):240-242 (2001).
Pardridge, W. M., "Drug transport across the blood-brain barrier," Journal of Cerebral Blood Flow & Metabolism, 32(11):1959-1972 (2012).
Pardridge, W. M. et al., "Transport of human recombinant brain-derived neurotrophic factor (BDNF) through the rat blood-brain barrier in vivo using vector-mediated peptide drug delivery," Pharmaceutical Research, 11(50:738-746 (1994).
Pardridge, W. M. et al., "Vector-mediated delivery of a polyamide ("peptide") nucleic acid analogue through the blood-brain barrier in vivo," Proc. Natl. Acad. Sci. USA, 92(12):5592-5596 (1995).
Parenti, G., "Treating lysosomal storage diseases with pharmacological chaperones: from concept to clinics," EMBO Mol. Med., 1:268-279 (2009).
Qian, Z. M. et al., "Targeted drug delivery via the transferrin receptor-mediated endocytosis pathway," Pharmacol. Rev., 54(4):561-587 (2002).
Richardson, D. R. et al., "The uptake of iron and transferrin by the human malignant melanoma cell," Biochimica et Biophysica Acta, 1053:1-12 (1990).
Robinson, L. J. et al., "NSF is required for transport from early to late endosomes," Journal of Cell Science, 110:2079-2087 (1997).
Rose, T. M. et al., "Primary Structure of the Human Melanoma-Associated Antigen P97 (Melanotransferrin) Deduced from the MRNA Sequence," Proc. Natl. Acad. Sci. USA, 83:1261-1265 (1986).
Saito, Y. et al., "Vector-mediated delivery of $^{125}$I-labeled beta-amyloid peptide Aβ1-40 through the blood-brain barrier and binding to Alzheimer's disease amytoid of the Aβ1-40/vector complex," Proc. Natl. Acad. Sci. USA, 92(22):10227-10231 (1995).
Sala, R. et al., "The Human Melanoma Associated Protein Melanotransferrin Promotes Endothelial Cell Migration and Angiogenesis in vivo," European Journal of Cell Biology, 81(11):599-607 (2002).

(56) References Cited

OTHER PUBLICATIONS

Sands, M. S., "Biodistribution, kinetics, and efficacy of highly phosphorylated and non-phosphorylated beta-glucuronidase in the murine model of mucopolysaccharidosis VII," Journal of Biological Chemistry, 276(46):43160-43165 (2001).

Shi, N. et al., "Noninvasive gene targeting to the brain," Proc. Natl. Acad. Sci. USA, 97(13):7567-7572 (2000).

Skarlatos, S. et al., "Transport of [125]transferrin through the rat blood-brain barrier," Brain Research, 683(2):164-171 (1995).

Song, B. W. et al., "Enhanced neuroprotective effects of basic fibroblast growth factor in regional brain ischemia after conjugation to a blood-brain barrier delivery vector," Journal of Pharmacology and Experimental Therapeutics, 301(2):605-610 (2002).

Srinivasachar, K. et al., "New protein cross-linking reagents that are cleaved by mild acid," Biochem. 28:2501-2509 (1989).

Stefano, J. E. et al., "In vitro and in vivo evaluation of a non-carbohydrate targeting platform for lysosomal proteins," Journal of Controlled Release, 135:113-118 (2009).

Tang, Y. et al., "Directing adenovirus across the blood-brain barrier via melanotransferrin (P97) transcytosis pathway in an vitro model," Gene Therapy, 14(6):523-532 (2007).

Thomas, F. C. et al., "Uptake of ANG1005, a novel paclitaxel derivative, through the blood-brain barrier into brain and experimental brain metastases of breast cancer," Pharmaceutical Research, 26(11):2486-2494 (2009).

WikiPedia Foundation, Inc., Sandhoff disease, http://en.wikipedia.org/wiki/Sandhof_disease, Modified 2007 (Printed Jan. 16, 2008).

Woodbury, R. G. et al., "Identification of a cell surface protein, p. 97, in human melanomas and certain other neoplasms," Proc. Natl. Acad. Sci. USA, 77(4):2183-2187 (1980).

Wu, D. et al., "Pharmacokinetics and brain uptake of biotinylated basic fibroblast growth factor conjugated to a blood-brain barrier drug delivery system," Journal of Drug Targeting, 10(3):239-245 (2002).

Wu, D. et al., "Central nervous system pharmacologic effect in conscious rate after intravenous injection of a biotinylated vasoactive intestinal peptide analog coupled to a blood-brain barrier drug delivery system," Journal of Pharmacology and Experimental Therapeutics, 279(1):77-83 (1996).

Wu, D. et al., "Pharmacokinetics and blood-brain barrier transport of [3H]-biotinylated phosphorothioate oligodeoxynucleotide conjugated to a vector-mediated drug delivery system," Journal of Pharmacology and Experimental Therapeutics, 276(1):206-211 (1996).

Yang, J. et al., "Deletion of the GPI pre-anchor sequence in human p97-a general approach for generating the soluble form of GPI-linked proteins," Protein Expression and Purification, 34(1):28-48 (2004).

Yoshikawa, T. et al., "Biotin delivery to brain with a covalent conjugate of avidin and a monoclonal antibody to the transferrin receptor," Journal of Pharmacology and Experimental Therapeutics, 263(2):897-903 (1992).

Zhang, Y. et al., "Conjugation of brain-derived neurotrophic factor to a blood-brain barrier drug targeting system enables neuroprotection in regional brain ischemia following intravenous injection of the neurotrophin," Brain Research, 889(1-2):49-56 (2001).

Shire Human Genetic Therapies, Inc., Lexington, MA, Idursulfase, U.S. Food and Drug Administration Product Label, 14 pages.

Shire Human Genetic Therapies, Inc., Lexington, MA, Idursulfase, European Medicines Evaluation Agency, 2007, 43 pages.

Office Action for U.S. Appl. No. 13/969,280, dated Sep. 18, 2015, 9 pages.

Office Action for U.S. Appl. No. 13/969,280, dated Aug. 29, 2016, 11 pages.

Office Action for U.S. Appl. No. 13/969,280, dated Apr. 13, 2016, 9 pages.

Office Action for U.S. Appl. No. 14/210,029, dated Jul. 27, 2015, 10 pages.

Office Action for U.S. Appl. No. 14/210,029, dated Jan. 25, 2016, 7 pages.

International Preliminary Report on Patentabiliy for International Application No. PCT/US2014/026620, dated Sep. 24, 2015, 10 pages.

Supplementary European Search Report for European Application No. 16166020.4, dated Aug. 18, 2016, 7 pages.

Office Action for U.S. Appl. No. 14/472,186, dated Mar. 4, 2016, 11 pages.

Office Action for U.S. Appl. No. 14/472,186, dated Oct. 13, 2016, 13 pages.

International Search Report and Written Opinion for International Application No. PCT/US2014/053257, dated Jun. 3, 2015, 22 pages.

International Search Report and Written Opinion for International Application No. PCT/US2015/014230, dated May 8, 2015, 12 pages.

International Search Report and Written Opinion for International Application No. PCT/US2015/015662, dated Jun. 10, 2015, 10 pages.

International Search Report and Written Opinion for International Application No. PCT/US2015/028743, dated Nov. 11, 2015, 20 pages.

Altenhofer, S. et al., "The NOX toolbox: validating the role of NADPH oxidases in physiology and disease," Cellular and Molecular Life Sciences, 69(14):2327-2343 (Jul. 2012). Epub May 31, 2012.

Catrina, A. et al., "Anti-tumour necrosis factor (TNF)-alpha therapy (etanercept) down-regulates serum matrix metalloproteinase (MMP)-3 and MMP-1 in rheumatoid arthritis," Rheumatology (Oxford), 41(5):484-489 (May 2002) (abstract only).

Costantino, L. et al., "Is there a clinical future for polymeric nanoparticles as brain-targeting drug delivery agents?", Drug Discovery Today, 17(7-8):367-378 (Apr. 2012). Epub Nov. 7, 2011.

Di Natale, P. et al., "Iduronate sulfatase from human placenta," Biochimica et Biophysica Acta, 839(3):258-261 (May 1985).

Gabathuler, R. et al., "BT2111, a new anticancer agent composed of trastuzumab and transcend a vector for brain delivery for the treatment of metastatic Her2+ breast cancer," [Abstract]. In: Proceedings of the AACR-NCI-EORTC International Conference: Molecular Targets and Cancer Therapeutics; Oct. 19-23, 2013; Boston, MA. Philadelphia (PA): AACR; Mol. Cancer Ther. 2013;12(11 Suppl.): Abstract nr A247.

Kohno, T. et al., P400, "Adalimumab and infliximab bind to FC-receptor and C1q and generate immunoprecipitation: a different mechanism from etanercept," J. Am. Acad. Dermatol., P36 (Mar. 2005), 1 page.

Millat, G. et al., "IDS transfer from overexpressing cells to IDS-deficient cells," Experimental Cell Research, 230(2):362-367 (Feb. 1997).

Starr, C. M. et al., "P97 sequence" SEQ ID No. 1, human P97 sequence, submitted in U.S. Appl. No. 12/729,792 (2010).

International Search Report and Written Opinion for International Application No. PCT/US2017/013410, dated Apr. 21, 2017, 11 pages.

Guo, H. H. et al., "Protein tolerance to random amino acid change," PNAS, 101(25):9205-9210 (Jun. 2004).

NCBI [online], "Cetuximab-MeSH," Retrieved on the Internet <URL: https://www.ncbi.nlm.nih.gov/mesh/?term=Erbitux>, Retrieved on Feb. 27, 2017, 2 pages.

Shao, W. et al., "Inhibition of human tumor xenograft growth in nude mice by a conjugate of monoclonal antibody LA22 to epidermal growth factor receptor with anti-tumor antibiotics mitomycin C," Biochemical and Biophysical Research Communications, 2006, 349:816-824.

\* cited by examiner

Amino Acid Sequence of Idursulfase

```
  1  Ser Gln Thr Gln Ala Asn Ser Thr Thr Asp Ala Leu Asn Val Leu Leu Ile Ile Val Asp
 21  Asp Leu Arg Pro Ser Leu Gly Cys Tyr Gly Asp Lys Leu Val Arg Ser Pro Asn Ile Asp
 41  Gln Leu Ala Ser His Ser Leu Leu Phe Gln Asn Ala Phe Ala Gln Gln Ala Val Cys Ala
 61  Pro Ser Arg Val Ser Phe Leu Thr Gly Arg Arg Pro Asp Thr Thr Arg Leu Tyr Asp Phe
 81  Asn Ser Tyr Trp Arg Val His Ala Gly Asn Phe Ser Thr Ile Pro Gln Tyr Phe Lys Glu
101  Asn Gly Tyr Val Thr Met Ser Val Gly Lys Val Phe His Pro Gly Ile Ser Ser Asn His
121  Thr Asp Asp Ser Pro Tyr Ser Trp Ser Phe Pro Pro Tyr His Pro Ser Ser Glu Lys Tyr
141  Glu Asn Thr Lys Thr Cys Arg Gly Pro Asp Gly Glu Leu His Ala Asn Leu Leu Cys Pro
161  Val Asp Val Leu Asp Val Pro Glu Gly Thr Leu Pro Asp Lys Gln Ser Thr Glu Gln Ala
181  Ile Gln Leu Leu Glu Lys Met Lys Thr Ser Ala Ser Pro Phe Phe Leu Ala Val Gly Tyr
201  His Lys Pro His Ile Pro Phe Arg Tyr Pro Lys Glu Phe Gln Lys Leu Tyr Pro Leu Glu
221  Asn Ile Thr Leu Ala Pro Asp Pro Glu Val Pro Asp Gly Leu Pro Pro Val Ala Tyr Asn
241  Pro Trp Met Asp Ile Arg Gln Arg Glu Asp Val Gln Ala Leu Asn Ile Ser Val Pro Tyr
261  Gly Pro Ile Pro Val Asp Phe Gln Arg Lys Ile Arg Gln Ser Tyr Phe Ala Ser Val Ser
281  Tyr Leu Asp Thr Gln Val Gly Arg Leu Leu Ser Ala Leu Asp Asp Leu Gln Leu Ala Asn
301  Ser Thr Ile Ile Ala Phe Thr Ser Asp His Gly Trp Ala Leu Gly Glu His Gly Glu Trp
321  Ala Lys Tyr Ser Asn Phe Asp Val Ala Thr His Val Pro Leu Ile Phe Tyr Val Pro Gly
341  Arg Thr Ala Ser Leu Pro Glu Ala Gly Glu Lys Leu Phe Pro Tyr Leu Asp Pro Phe Asp
361  Ser Ala Ser Gln Leu Met Glu Pro Gly Arg Gln Ser Met Asp Leu Val Glu Leu Val Ser
381  Leu Phe Pro Thr Leu Ala Gly Leu Ala Gly Leu Gln Val Pro Pro Arg Cys Pro Val Pro
401  Ser Phe His Val Glu Leu Cys Arg Glu Gly Lys Asn Leu Leu Lys His Phe Arg Phe Arg
421  Asp Leu Glu Glu Asp Pro Tyr Leu Pro Gly Asn Pro Arg Glu Leu Ile Ala Tyr Ser Gln
441  Tyr Pro Arg Pro Ser Asp Ile Pro Gln Trp Asn Ser Asp Lys Pro Ser Leu Lys Asp Ile
461  Lys Ile Met Gly Tyr Ser Ile Arg Thr Ile Asp Tyr Arg Tyr Thr Val Trp Val Gly Phe
481  Asn Pro Asp Glu Phe Leu Ala Asn Phe Ser Asp Ile His Ala Gly Glu Leu Tyr Phe Val
501  Asp Ser Asp Pro Leu Gln Asp His Asn Met Tyr Asn Asp Ser Gln Gly Gly Asp Leu Phe
521  Gln Leu Leu Met Pro
```

Asn - marks sites of N-linked glycosylation

Figure 6

DEPHOSPHORYLATED LYSOSOMAL STORAGE DISEASE PROTEINS AND METHODS OF USE THEREOF

CROSS-REFERENCE TO RELATED APPLICATIONS

This application claims priority under 35 U.S.C. § 119(e) to U.S. Provisional Application No. 61/677,959, filed Jul. 31, 2012, which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is BIOS_006_01US_ST25.txt. The text file is about 25 KB, was created on Jul. 31, 2013, and is being submitted electronically via EFS-Web.

BACKGROUND

Technical Field

The present invention relates generally to dephosphorylated forms of lysosomal storage disease (LSD) proteins, including dephosphorylated forms of iduronate-2-sulfatase (IDS, or I2D), having increased ability to traverse or penetrate the blood brain barrier (BBB) relative to phosphorylated forms of the protein, and p97 conjugates thereof. Also included are compositions comprising such dephosphorylated LSD proteins and p97 conjugates, and methods of use thereof, for instance, to treat any one or more lysosomal storage diseases, such as Hunter Syndrome (or MPS Type II).

Description of the Related Art

Lysosomal storage diseases (LSDs) result from the absence or reduced activity of specific enzymes or proteins within the lysosomes of a cell. Within cells, the effect of the missing enzyme can be seen as an accumulation of un-degraded "storage material" within the intracellular lysosome. This build-up causes lysosomes to swell and malfunction, resulting in cellular and tissue damage. As lysosomal storage diseases typically have a genetic etiology, many tissues will lack the enzyme in question. However, different tissues suffer the absence of the same enzyme differently. How adversely a tissue will be affected is determined, to some extent, by the degree to which that tissue generates the substrate of the missing enzyme. The types of tissue most burdened by storage, in turn, dictate how the drug should be administered to the patient.

A large number of lysosomal storage disease enzymes have been identified and correlated with their respective diseases. Once the missing or deficient enzyme has been identified, treatment can focus on the problem of effectively delivering the replacement enzyme to a patient's affected tissues.

Intravenous enzyme replacement therapy (ERT) can be beneficial for LSDs (e.g., MPS I, MPS II, MPS III); however, means for enhancing the delivery of the therapeutic enzyme to the lysosome in such diseases would be advantageous in terms of reduced cost and increased therapeutic efficacy.

As one problem, the blood-brain barrier (BBB) blocks the free transfer of many agents from blood to brain. For this reason, LSDs that present with significant neurological aspect are not expected to be as responsive to intravenous ERT. For such diseases, methods of improving the delivery of the enzyme across the BBB and into the lysosomes of the affected cells would be highly desirable.

BRIEF SUMMARY OF THE INVENTION

Embodiments of the present invention include isolated lysosomal storage disease (LSD) polypeptides that are substantially dephosphorylated, relative to a corresponding control LSD protein expressed (or produced) in a mammalian cell, such as a human cell. In certain embodiments, the LSD polypeptide is at least about 75%, 80%, 90%, 95%, 98%, 99%, or 100% dephosphorylated, relative to the corresponding LSD protein.

In particular embodiments, the LSD polypeptide comprises one or more N-linked oligomannose glycans. For instance, certain LSD polypeptides comprises 1, 2, 3, 4, 5, 6, 7, 8, 9, or 10 or more N-linked oligomannose glycans. In some embodiments, the LSD polypeptide has at least about 75%, 80%, 90%, 95%, 98%, 99%, or 100% of the number or amount of N-linked oligomannose glycans as the corresponding LSD protein. In particular embodiments, the LSD polypeptide is substantially free of mannose-6-phosphate (M6P) residues of the N-linked oligomannose glycan(s), relative to a corresponding LSD protein expressed (or produced) in a mammalian cell. In some aspects, the LSD polypeptide is dephosphorylated by enzymatic digestion with an acid phosphatase or an alkaline phosphatase.

In certain embodiments, the LSD polypeptide is selected from one or more of iduronate-2-sulfatase, L-iduronidase, aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, heparan-N-sulfatase, α-N-acetylglucosaminidase, acetyl-CoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter, including active fragments and variants thereof. In some embodiments, the LSD polypeptide is a human polypeptide.

In some embodiments, the LSD polypeptide is human iduronate-2-sulfatase (IDS), or an active fragment or variant thereof. In some aspects, the human IDS has an amino acid sequence that is at least 80%, 85%, 90%, 95%, 98%, 99%, or 100% identical to SEQ ID NO:2, or comprises, consists essentially of, or consists of SEQ ID NO:2. In some aspects, the human IDS comprises one or more N-linked oligomannose glycans. In particular aspects, the human IDS comprises 1, 2, 3, 4, 5, 6, 7, or 8 N-linked oligomannose glycans. In some aspects, the human IDS has at least about 75%, 80%, 85%, 90%, 95%, 98%, 99%, or 100% of the number or amount of N-linked oligomannose glycans as a corresponding wild-type human iduronate-2-sulfatase produced (expressed) in a mammalian cell, such as a human cell (e.g., HT-1080 cell). In some embodiments, the one or more N-linked oligomannose glycans are substantially dephosphorylated, relative to the N-linked oligomannose glycans of corresponding human IDS produced (expressed) in a mammalian cell, such as a human cell. In some aspects, the one or more N-linked oligomannose glycans are at least about 75%, 80%, 85%, 90%, 95%, 98%, 99%, or 100% dephosphorylated.

In some embodiments, the human IDS is substantially free of mannose-6-phospate (M6P) residues, relative to the corresponding IDS produced in a mammalian cell. In particular aspects, the human IDS comprises a M6P content of less than about 1.2 pmol M6P/pmol IDS protein. In certain aspects, the human IDS comprises a M6P content of less than about 0.5 pmol M6P/pmol IDS protein. In specific aspects, the human IDS comprises a M6P content of about or less than about 0.15 pmol M6P/pmol IDS protein.

In some embodiments, the LSD polypeptide is human α-L-iduronidase (IDU), or an active fragment or variant thereof. In some aspects, the human IDU has an amino acid sequence that is at least 80%, 85%, 90%, 95%, 98%, 99%, or 100% identical to SEQ ID NO:3, or comprises, consists essentially of, or consists of SEQ ID NO:3. In some aspects, the human IDU comprises one or more N-linked oligomannose glycans. In particular aspects, the human IDU comprises 1, 2, 3, 4, 5, or 6 N-linked oligomannose glycans. In some embodiments, the human IDU has at least about 75%, 80%, 85%, 90%, 95%, 98%, 99%, or 100% of the number or amount of N-linked oligomannose glycans as a corresponding human IDU produced (expressed) in a mammalian cell, optionally a human cell. In particular aspects, the one or more N-linked oligomannose glycans are substantially dephosphorylated, relative to the N-linked oligomannose glycans of corresponding human IDU produced (expressed) in a mammalian cell, optionally a human cell. In specific aspects, the one or more N-linked oligomannose glycans are at least 75%, 80%, 85%, 90%, 95%, 98%, 99%, or 100% dephosphorylated. In some aspects, the human IDU is substantially free of mannose-6-phospate (M6P) residues, relative to the corresponding IDU produced in a mammalian cell.

In certain embodiments, the corresponding protein is a wild-type protein, such as a human wild-type IDS or IDS protein. In specific embodiments, the corresponding protein for substantially dephosphorylated IDS is idursulfase produced in a human cell line, optionally the HT-1080 fibrosarcoma cell line.

In some embodiments, the mammalian cell is selected from a CHO cell, an HEK293 cell, a HeLa cell, and a HT-1080 fibrosarcoma cell.

Also included are conjugates, comprising a p97 polypeptide that is covalently or operatively linked to an a substantially dephosphorylated LSD polypeptide described herein, to form a p97 conjugate.

Also included are compositions, including pharmaceutical compositions, comprising an isolated lysosomal storage disease (LSD) polypeptide or p97 conjugate described herein. In some embodiments, the composition comprises a pharmaceutically acceptable carrier.

Certain embodiments include methods of treating a lysosomal storage disease (LSD) in subject in need thereof, comprising administering to the subject a composition (e.g., pharmaceutical composition), substantially dephosphorylated LSD protein, or conjugate described herein.

In certain methods, the LSD is selected from one or more of mucopolysaccharidosis type II (Hunter Syndrome), mucopolysaccharidosis type I (Hurler Syndrome), aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leucodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leucodystrophy, mucolipidosis type I, sialidosis types I/II mucolipidosis types II/III I-cell disease, mucolipidosis type IIIC pseudo-Hurler polydystrophy, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types NB, Niemann-Pick disease, Niemann-Pick disease type C1, Niemann-Pick disease type C2, pycnodysostosis, Schindler disease types I/II, Schindler disease, and sialic acid storage disease.

In specific embodiments, the LSD is mucopolysaccharidosis type II (Hunter syndrome), and the substantially dephosphorylated LSD protein is human iduronate-2-sulfatase.

In other embodiments, the LSD is mucopolysaccharidosis type I (Hurler Syndrome), and the substantially dephosphorylated LSD protein is human L-iduronidase.

In some embodiments, the LSD has central nervous system (CNS) involvement, or the subject is at risk for developing CNS involvement of the LSD.

Also included are methods of producing a substantially dephosphorylated LSD protein, such as human iduronate-2-sulfatase (IDS), comprising recombinantly producing the LSD protein in a mammalian cell line, optionally a human cell line, and treating the recombinantly produced LSD protein with a phosphatase for a time sufficient to reduce the mannose-6-phosphate (M6P) content of the LSD protein by at least about 50%, 60%, 70%, 80%, 90%, 95%, 98%, or 99%, relative to untreated LSD protein produced in the same cell line. In particular embodiments, the LSD protein is human IDS or human IDU.

In particular embodiments, the human cell line is a HT-1080 fibrosarcoma cell line, and the protein is human IDS. In some aspects, the human IDS comprises or consists of the amino acid sequence of SEQ ID NO:2. In particular aspects, the phosphatase is a calf intestine alkaline phosphatase (CIP). In specific aspects, the CIP is bound to acrylic beads.

In some embodiments, the LSD protein, such as human IDS, is fused to a human p97 sequence. Certain methods further comprise conjugating the LSD protein, such human IDS, to a human p97 polypeptide.

Specific embodiments include an isolated human iduronate-2-sulfatase (IDS) polypeptide, where the human IDS polypeptide comprises or consists of the amino acid sequence of SEQ ID NO:2, or a variant thereof, and where the mannose-6-phosphate (M6P) content is less than about 1.2 pmol M6P/pmol IDS protein. In particular aspects, the M6P content is less than about 0.5 pmol M6P/pmol IDS protein. In some aspects, the M6P content is about or less than about 0.15 pmol M6P/pmol IDS protein.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6 shows the amino acid sequence of idursulfase (human IDS) (SEQ ID NO:2), and indicates N-linked glycosylation sites.

DETAILED DESCRIPTION OF THE INVENTION

Figure 1:
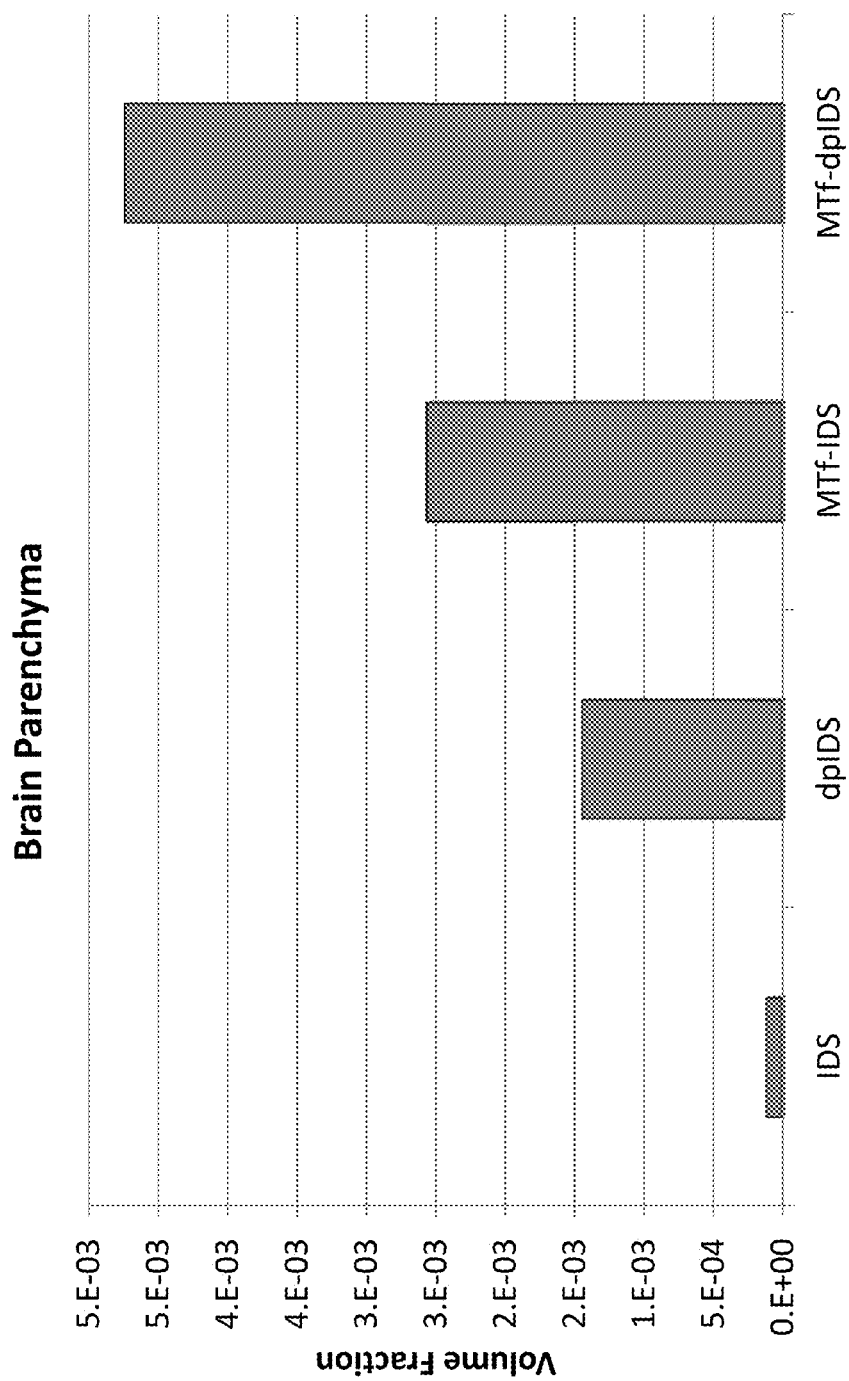
FIG. 1 shows the levels of test proteins accumulated in the brain parenchyma of mice following intravenous injection (IDS, iduronate-2-sulfatase; dpIDS, dephosphorylated iduronate-2-sulfatase; MTf-IDS, p97-IDS conjugate; MTf-dpIDS, p97-dpIDS conjugate).

Embodiments of the present invention are based partly on the discovery that dephosphorylated forms of lysosomal storage disease (LSD) proteins such as iduronate-2-sulfatase (IDS) have significantly increased ability to transfer across the blood brain barrier (BBB) and into central nervous system (CNS) tissues, relative to normally phosphorylated proteins. Conjugation to p97 (melanotransferrin) polypeptide sequences can further improve the transfer of dephosphorylated LSD proteins across the BBB and into CNS tissues.

Many lysosomal enzymes are targeted to lysosomes by a specialized trafficking pathway that involves the generation of phosphorylated N-glycans. The phosphorylation step typically occurs in the cis-Golgi and involves the transfer of GlcNAc-1-P to C-6 of mannose residues of oligomannose N-linked glycans. A glycosidase in the trans-Golgi removes the N-acetylglucosamine to generate mannose-6-phosphate residues. Such residues are recognized by lectin receptors (mannose-6-phosphate receptors) that transport the lysosomal enzyme into an acidified compartment where it is released from the receptor and ultimately ends up in a lysosome. Here, it has been unexpectedly found that removal of phosphate groups from oligomannose N-linked glycans, for instance, by incubation with an acid phosphatase, alters the pharmacokinetics of LSD proteins such as iduronate-2-sulfatase, in a way that increases transfer across the BBB but still allows sufficient trafficking to lysosomal compartments within cells of the central nervous system.

Accordingly, the dephosphorylated LSD proteins described herein and related p97 conjugates can find a variety of uses in the improved treatment of lysosomal storage diseases (LSDs) by enzyme replacement therapy (ERT), including but not limited to those LSDs having or at risk for having a nervous system or CNS component. In particular embodiments, the LSD protein is a substantially dephosphorylated version of IDS that is optionally conjugated to a human p97 polypeptide, which can be used, for instance, to improve the treatment of Hunter Syndrome, relative to ERT that uses normally phosphorylated protein. In other embodiments, the LSD protein is a substantially dephosphorylated version of IDU that is optionally conjugated to a human p97 polypeptide, which can be used, for instance, to improve the treatment of Hurler Syndrome, relative to ERT that uses normally phosphorylated protein.

Other advantages and benefits will be apparent to persons skilled in the art.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent or non-covalent attachment or linkage of an agent or other molecule, e.g., a biologically active molecule, to a p97 polypeptide. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

As used herein, the terms "function" and "functional" and the like refer to a biological, enzymatic, or therapeutic function.

Figure 3:
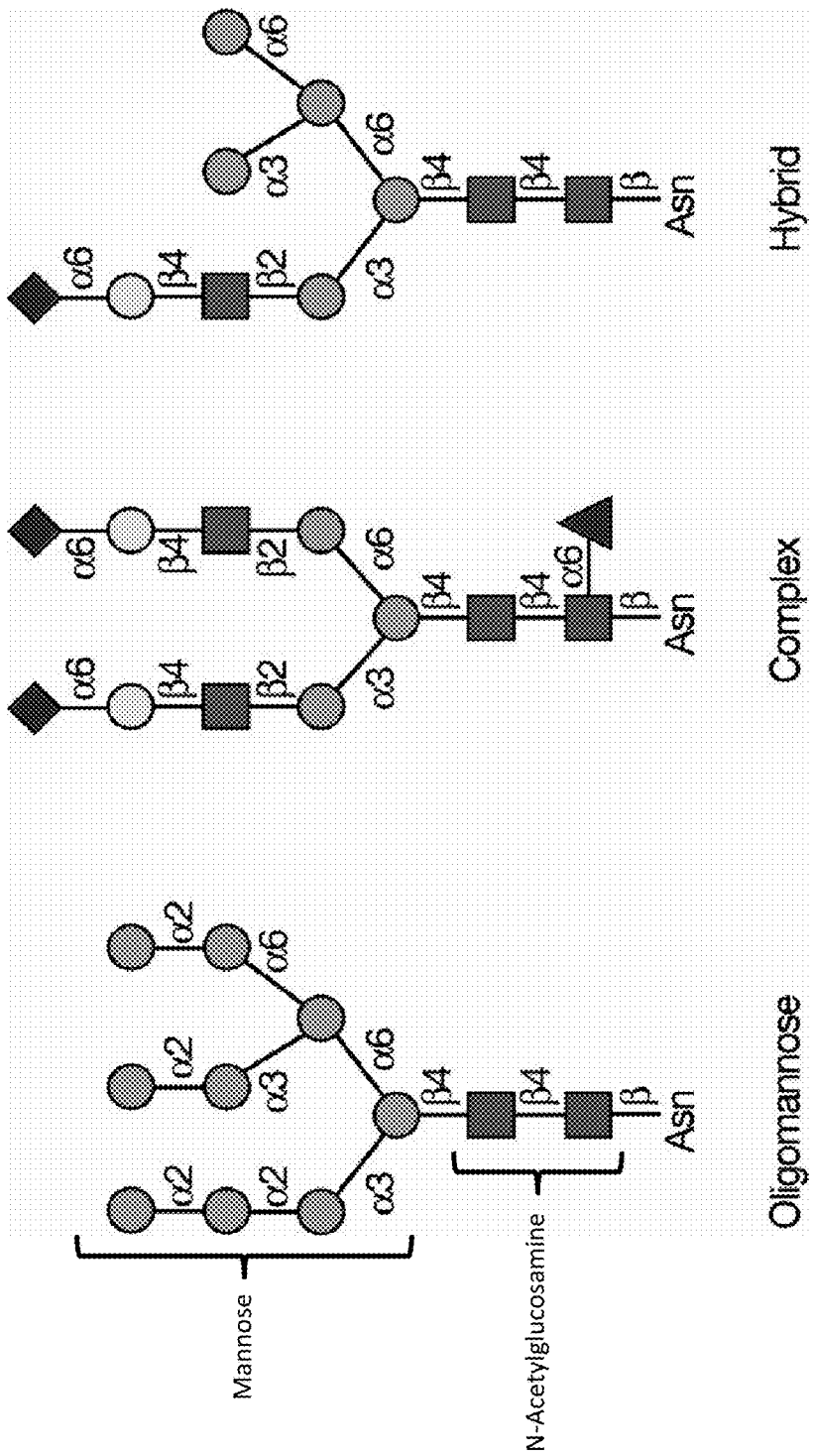
FIG. 3 shows three types of N-linked glycans: oligomannose glycans, in which only mannose residues are attached to the core; complex glycans, in which N-acetylglucosaminyltransferases (GlcNAcTs) are attached to the core; and hybrid glycans, in which only mannose residues are attached to the Manα1-6 arm of the core and one or two antennae are on the Manα1-3 arm.
Figure 4:
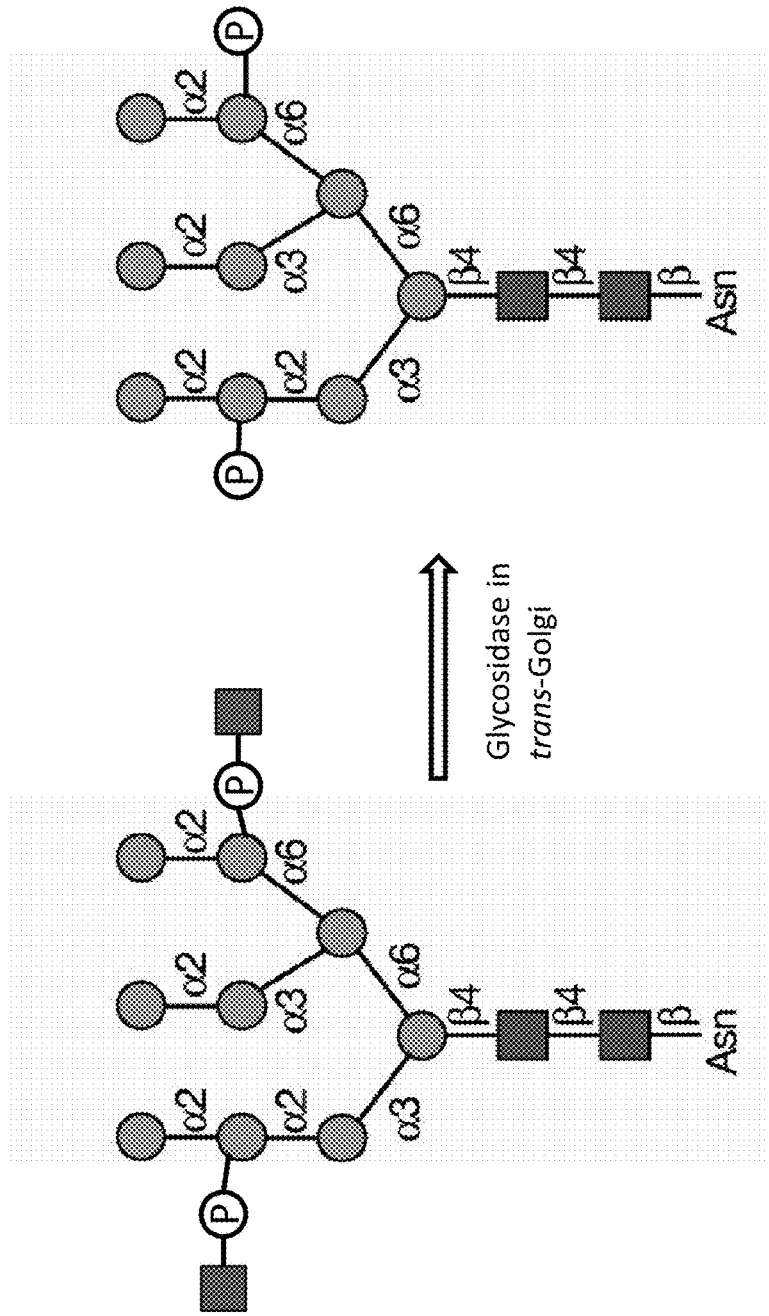
FIG. 4 illustrates the production of lysosomal proteins that acquire a GlcNAc-1-P at C-6 of mannose residues on oligomannose N-glycans in the cis-Golgi; the N-acetylglucosamine is removed in the trans-Golgi by a glycosidase to expose the phosphate residues.

The term "glycan" refers to a polysaccharide or oligosaccharide that usually includes O-glycosidic linkages of monosaccharides. Glycans can be homo- or heteropolymers of monosaccharide residues, and/or they can be linear or branched. Glycosylation includes the co-translational or post-translational reaction in which a glycan is attached to a functional group of protein. Examples of protein-associated glycans include N-linked glycans, O-linked glycans, phosphoglycans, C-linked glycans, and glycophosphatidylinositol (GPI)-anchors. N-linked glycans are attached to a nitrogen of asparagine or arginine side-chains, and O-linked glycans are attached to the hydroxy oxygen of serine, threonine, tyrosine, hydroxylysine, or hydroxyproline side-chains. N-linked glycans share a common core sugar sequence, Manα1-6(Manα1-3)Manβ1-4GlcNAcβ1-4GlcNAcβ1-Asn-X-Ser/Thr, and are classified into three types: (1) oligomannose, in which only mannose residues are attached to the core; (2) complex, in which "antennae" initiated by N-acetylglucosaminyltransferases (GlcNAcTs) are attached to the core; and (3) hybrid, in which only mannose residues are attached to the Manα1-6 arm of the core and one or two antennae are on the Manα1-3 arm (see FIG. 3). FIG. 4 illustrates the production of lysosomal proteins (e.g., LSD proteins) that acquire a GlcNAc-1-P at C-6 of mannose residues on oligomannose N-glycans in the cis-Golgi; the N-acetyl-glucosamine is removed in the trans-Golgi by a glycosidase, thereby exposing mannose-6-phosphate residues that are recognized by a mannose-6-phosphate receptor and routed to an acidified, pre-lysosomal compartment.

"Homology" refers to the percentage number of amino acids that are identical or constitute conservative substitutions. Homology may be determined using sequence comparison programs such as GAP (Deveraux et al., *Nucleic Acids Research*. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "linkage," "linker," "linker moiety," or "l" is used herein to refer to a linker that can be used to separate a p97 polypeptide fragment from an agent of interest, or to separate a first agent from another agent, for instance where two or more agents are linked to form a p97 conjugate. The linker may be physiologically stable or may include a releasable linker such as an enzymatically degradable linker (e.g., proteolytically cleavable linkers). In certain aspects, the linker may be a peptide linker, for instance, as part of a p97 fusion protein. In some aspects, the linker may be a non-peptide linker or non-proteinaceous linker. In some aspects, the linker may be particle, such as a nanoparticle.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of polypeptide of conjugate of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the activity, such as the amount or rate of transport/delivery across the blood brain barrier, the rate and/or levels of distribution to central nervous system tissue, and/or the $C_{max}$ for plasma, central nervous system tissues, or any other systemic or peripheral non-central nervous system tissues, of a substantially dephosphorylated (dp) lysosomal storage protein described herein relative to a normally phosphorylated version of that protein, or of a p97-polypeptide conjugate relative to the polypeptide alone. Other examples of comparisons and "statistically significant" amounts are described herein.

In certain embodiments, the "purity" of any given polypeptide (e.g., a substantially dephosphorylated LSD protein, a p97 conjugate) in a composition may be specifically defined. For instance, certain compositions may comprise a polypeptide that is at least 80%, 85%, 90%, 91%, 92%, 93%, 94%, 95%, 96%, 97%, 98%, 99%, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" and "enzyme" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Ha), as the driving force. For purposes herein, a "releasable linker" is synonymous with a "degradable linker." An "enzymatically degradable linkage" includes a linkage, e.g., amino acid sequence, that is subject to degradation by one or more enzymes, e.g., peptidases or proteases. In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or less.

The term "reference sequence" refers generally to a nucleic acid coding sequence, or amino acid sequence, to which another sequence is being compared. All polypeptide and polynucleotide sequences described herein are included as references sequences, including those described by name and those described in the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, H is, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of an agent such as a polypeptide to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, a substantially dephosphorylated LSD protein or a p97 conjugate has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom, or is at risk for exhibiting a symptom, which can be treated or diagnosed with a substantially dephosphorylated LSD protein or a p97 conjugate of the invention. Suitable subjects (patients) include laboratory animals (such as mouse, rat, rabbit, or guinea pig), farm animals, and domestic animals or pets (such as a cat or dog). Non-human primates and, preferably, human patients, are included. In particular embodiments, the subject has a lysosomal storage disorder, such as Hunter Syndrome.

"Substantially" or "essentially" means nearly totally or completely, for instance, about 70%, 75%, 80%, 85%, 90%, 95%, 96%, 97%, 98%, 99% or greater of some given quantity. In some aspects, a lysosomal storage disorder protein is substantially dephosphorylated, for example, relative to a corresponding wild-type protein produced in mammalian cells (e.g., human cells).

"Substantially free" refers to the nearly complete or complete absence of a given quantity for instance, less than about 30%, 25%, 20%, 15%, 10%, 5%, 4%, 3%, 2%, 1%, 0.5% or less of some given quantity. For example, certain compositions may be "substantially free" of cell proteins, membranes, nucleic acids, endotoxins, or other contaminants. In some aspects, a lysosomal storage disorder protein is "substantially free" of phosphate groups.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

Substantially Dephosphorylated Lysosomal Storage Disorder Proteins

As noted above, embodiments of the present invention include substantially dephosphorylated lysosomal storage disorder (LSD) proteins, or lysosomal proteins that associate with one or more lysosomal storage diseases. Examples include lysosomal hydrolases and other lysosomal enzymes that metabolize waste materials and cellular debris such as lipids, glycoproteins, and mucopolysaccharides, transmembrane proteins, soluble nonenzymatic proteins, membrane transport proteins, and proteins that post-translationally modify enzymes.

Exemplary lysosomal or LSD proteins include iduronate-2-sulfatase, L-iduronidase, aspartylglucosaminidase, acid lipase, cysteine transporter, Lamp-2, α-galactosidase A, acid ceramidase, α-L-fucosidase, β-hexosaminidase A, GM2-ganglioside activator (GM2A), α-D-mannosidase, β-D-mannosidase, arylsulfatase A, saposin B, neuraminidase, α-N-acetylglucosaminidase phosphotransferase, phosphotransferase γ-subunit, heparan-N-sulfatase, α-N-acetylglucosaminidase, acetylCoA:N-acetyltransferase, N-acetylglucosamine 6-sulfatase, galactose 6-sulfatase, β-galactosidase, N-acetylgalactosamine 4-sulfatase, hyaluronoglucosaminidase, sulfatases, palmitoyl protein thioesterase, tripeptidyl peptidase I, acid sphingomyelinase, cathepsin A, cathepsin K, α-galactosidase B, NPC1, NPC2, sialin, and sialic acid transporter. In particular embodiments, the LSD protein is a human protein.

In certain embodiments, the substantially dephosphorylated LSD protein is at least about 50%, 55%, 60%, 65%, 70%, 75%, 80%, 85%, 90%, 95%, 98%, 99%, or 100% (i.e., fully) dephosphorylated, relative to a corresponding control LSD protein.

In some embodiments, the substantially dephosphorylated LSD protein is substantially free of phosphate groups, for instance, the LSD protein has less than about 1%, 2%, 5%, 10%, 15%, 20%, 25%, 30%, 35%, 40%, 45%, or 50% of the phosphate groups of a corresponding control LSD protein. Alterations in protein phosphorylation can be measured according to routine techniques in the art, such as SDS-PAGE analysis to measure overall molecular weight, isotope labeling and mass spectrometry (see Bonenfant et al., *PNAS USA*. 100:880-885, 2003); Western blotting and ELISA using phosphoprotein-specific antibodies; and quantitative analysis of protein phosphorylation status using fluorescent phosphorylation sensor dyes (see Pro-Q Diamond® dye from Molecular Probes).

A corresponding "control" protein includes a protein of the same type (e.g., same protein name from same genus and/or species, same or nearly identical amino acid sequence), which has been recombinantly produced in a mammalian cell (e.g., human cell) with normal or wild-type glycosylation and phosphorylation machinery (e.g., CHO cells, HEK cells), and which preferably has not been treated, for instance, with an enzyme such as a glycosidase or a phosphatase. In some aspects, the corresponding control protein is a wild-type version of the substantially dephosphorylated LSD protein. In specific embodiments, for instance, where the LSD protein is iduronate-2-sulfatase, the corresponding control protein is idursulfase (Elaprase®) produced in a human cell, such as the HT-1080 human fibrosarcoma cell line (see Garcia et al., *Mol. Genet. Metab.* 91: 183-90, 2007; and FIG. 5).

Dephosphorylated LSD proteins can be prepared according to a variety of techniques in the art. For instance, because many phosphate groups are associated with mannose-6-phosphate residues on N-linked oligomannose glycans, reducing the number of glycans or degree of glycosylation on an LSD protein can likewise reduce the number of phosphate groups or the degree of phosphorylation. Reduced levels of glycan-associated phosphorylation can thus be achieved, for instance, by mutating one or more residues associated with potential glycosylation sites (e.g., residues in N-linked glycosylation sites such as Asn-X-Ser or Asn-X-Thr where X is any amino acid except Pro), by enzymatic deglycosylation (e.g., treatment with Peptide-N-Glycosidase F (PNGase F), mannosidase), by manipulation of cell culture media or cell culture conditions to inhibit N-glycan processing, and/or by recombinant production of LSD proteins in mammalian, yeast, insect, or other cell types having altered, reduced, or no glycosylation capabilities (see, e.g., Hossler et al., *Glycobiology.* 19:936-949, 2009; and Cummings and Esko et al., editors, *Essentials of Glycobiology.* 2$^{nd}$ Edition, Cold Spring Harbor Laboratory Press, 2009, including Chapters 8, 46, and 50). Examples of cells having significantly reduced glycosylation capabilities include many bacteria, such as *E. coli*.

In certain instances, however, it is preferable to reduce the phosphorylation of an LSD protein without significantly reducing its glycosylation state, that is, without significantly reducing the number or amount of glycans, including N-linked oligomannose glycans. Hence, in certain embodiments, an LSD protein is substantially dephosphorylated relative to a corresponding control protein, but has the same or substantially the same number of glycans or degree of glycosylation as the control protein. In particular embodiments, the substantially dephosphorylated LSD protein has the same or substantially the same number or degree of N-linked oligomannose glycans as the corresponding control protein. Examples include where the substantially dephosphorylated LSD protein has at least about 50%, 55%, 60%, 65%, 70%, 75%, 80%, 85%, 90%, 95%, 98%, 99%, or 100% of the number of glycans (e.g., N-linked oligomannose glycans) or degree of glycosylation as the corresponding control protein. Glycosylation states can be measured according to a variety of techniques in the art, such as SDS-PAGE analysis to measure overall molecular weight, fluorescent 2-D gel-based methods coupled with enzymatic pre-treatment of proteins with PNGase F (Peptide: N-Glycosidase F) and fluorescent 2-D gels or 2-D gel Western blotting (see Graham et al., *Proteomics.* 8:4919-30, 2008), and mass spectrometric-based methods for quantitating N-linked glycoproteins (see Rebecchi et al., *Current Proteomics.* 8:269-277(9), 2011).

In these and related embodiments, the glycans in particular (e.g., N-linked oligomannose glycans; see FIG. 4) can be substantially dephosphorylated relative to the glycans of a corresponding control protein. For example, in certain embodiments, the glycans (e.g., N-linked oligomannose glycans) of the LSD protein are at least about 50%, 55%, 60%, 65%, 70%, 75%, 80%, 85%, 90%, 95%, 98%, 99%, or 100% (i.e., fully) dephosphorylated, relative to the glycans of a corresponding control LSD protein. In some aspects, the glycans (e.g., N-linked oligomannose glycans) of the LSD protein are substantially free of phosphate groups, for instance, by having less than about 1%, 2%, 5%, 10%, 15%, 20%, 25%, 30%, 35%, 40%, 45%, or 50% of the phosphate groups of the glycans of a corresponding control LSD protein. In certain embodiments, the substantially dephosphorylated LSD protein is substantially free of mannose-6-phosphate (M6P) residues, for instance, by having less than about 1%, 2%, 5%, 10%, 15%, 20%, 25%, 30%, 35%, 40%, 45%, or 50% of the M6P residues of a corresponding control LSD protein.

In some embodiments, a glycosylated and phosphorylated LSD protein can be produced in mammalian or other cells, and then treated in vitro with one or more phosphatases to reduce the number of phosphate groups (e.g., mannose-6-phosphate residues associated with N-linked oligomannose glycans), optionally without significantly reducing the number of glycans or degree of glycosylation (see Example 1). General examples of phosphatases include acid phosphatases and alkaline phosphatases. Examples of acid phosphatases include prostatic acid phosphatase, lysosomal acid phosphatase, erythrocytic acid phosphatase, macrophage acid phosphatase, osteoclastic acid phosphates, and potato acid phosphatase. Examples of commonly employed alkaline phosphatases include shrimp alkaline phosphatase, calf-intestinal alkaline phosphatase, placental alkaline phosphatase, and secreted alkaline phosphatase (i.e., a C-terminal truncation of placental alkaline phosphatase).

In some aspects, the substantially dephosphorylated LSD protein is human iduronidase (α-L-iduronidase; IDU), or an active fragment or variant thereof. Iduronidase is an lysosomal enzyme involved in the degeneration of glycosaminoglycans such as dermatan sulfate and heparan sulfate, and its deficiency is associated with MPS I, or Hurler Syndrome. SEQ ID NO:3 provides the primary amino acid sequence of human iduronidase.

Human IDU has six potential N-linked glycosylation sites, mainly "complex type" oligosaccharides, at least two of which have been shown to be mannose-6-phosphorylated (see Brooks et al., *Glycobiology.* 11:741-750, 2001; and Zhao et al., *J. Biol. Chem.* 272:22758-22765:1997). In some embodiments, a substantially dephosphorylated human IDU has mutations at one or more of these glycosylation sites, to reduce N-linked glycans and their associated mannose-6-phosphate residues. Hence, in these and related embodiments, a human IDU protein is both substantially deglycosylated (e.g., of N-linked oligomannose glycans) and substantially dephosphorylated, relative to a wild-type human IDU protein.

In specific aspects, the substantially dephosphorylated LSD protein is human iduronate-2-sulfatase (IDS), or an active fragment or variant thereof. IDS (iduronate-2-sulfatase; EC 3.1.6.13) is a lysosomal exo-sulfatase that is involved in the degradation of the glycosaminoglycans heparan sulfate and dermatan sulfate. An IDS deficiency causes the lysosomal storage disorder MPS II (mucopolysaccharidosis type II). SEQ ID NO:2 provides the primary amino acid sequence of human IDS (idursulfase). Also included are glycosylation variants of human IDS (see U.S. Pat. Nos. 5,798,239 and 5,932,211), which have been substantially dephosphorylated, as described herein.

The human IDS sequence contains eight potential N-linked glycosylation sites (i.e., NXS/T motifs) at positions 31, 115, 144, 246, 280, 325, 513 and 537 (see Parkinson-Lawrence et al., Biochem J. 386:395-400, 2005; and FIG. 6 for corresponding N-linked glycosylation sites in SEQ ID NO:2). In some embodiments, a substantially dephosphorylated human IDS has mutations at one or more of these glycosylation sites, to reduce N-linked glycans and their associated mannose-6-phosphate residues. Hence, in these and related embodiments, a human IDS protein is both substantially deglycosylated (e.g., of N-linked oligomannose glycans) and substantially dephosphorylated, relative to a wild-type human IDS protein.

In other aspects, a substantially dephosphorylated human IDU or IDS protein has the same or substantially the same number of glycans or degree of glycosylation as a corresponding control human IDS or IDU protein (e.g., wild-type protein). For instance, the substantially dephosphorylated human IDU or IDS protein may have N-linked glycans (e.g., oligomannose glycans) at 1, 2, 3, 4, 5, 6, 7, or 8 of the potential N-linked glycosylation sites. The human IDU or IDS protein may thus have at least about 50%, 55%, 60%, 65%, 70%, 75%, 80%, 85%, 90%, 95%, 98%, 99%, or 100% of the number or amount of N-linked oligomannose glycans as a corresponding wild-type human IDU or IDS produced (expressed) in a mammalian cell, optionally a human cell. In specific aspects, the one or more N-linked oligomannose glycans of human IDU or IDS are substantially dephosphorylated, relative to the N-linked oligomannose glycans of the corresponding control human IDU or IDS protein. For instance, the one or more N-linked oligomannose glycans of human IDU or IDS can be at least 50%, 55%, 60%, 65%, 70%, 75%, 80%, 85%, 90%, 95%, 98%, 99%, or 100% (i.e., fully) dephosphorylated, relative to corresponding control human IDS protein. In some aspects, the one or more N-linked oligomannose glycans of human IDU or IDS are substantially free of phosphate groups, for instance, the glycans of the dephosphorylated IDU or IDS protein have less than about 1%, 2%, 5%, 10%, 15%, 20%, 25%, 30%, 35%, 40%, 45%, or 50% of the phosphate groups of the glycans of a corresponding control human IDU or IDS protein. In certain embodiments, the substantially dephosphorylated IDU or IDS protein is substantially free of mannose-6-phosphate (M6P) residues, for instance, by having less than about 1%, 2%, 5%, 10%, 15%, 20%, 25%, 30%, 35%, 40%, 45%, or 50% of the M6P residues of a corresponding control IDU or IDS protein. In specific embodiments, the substantially dephosphorylated IDS protein has M6P content of about or less than about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.3, 1.4, or 1.5 pmol M6P/pmol IDS protein, including all ranges and integers in between.

In specific embodiments, the human IDS protein is a substantially dephosphorylated form of idursulfase (Elaprase®), produced in a human cell (e.g., HT-1080 cell), which has been treated with one or more phosphatases (e.g., acid phosphatase, alkaline phosphatase) to reduce the number of phosphate groups or M6P residues thereon.

p97 Polypeptide Sequences and Conjugates Thereof

Embodiments of the present invention also include conjugates that comprise a human p97 (melanotransferrin; MTf) polypeptide that is coupled, linked or otherwise attached to a dephosphorylated LSD protein described herein, compositions that comprise such conjugates, and related methods of use thereof.

In particular embodiments, the p97 polypeptide is covalently, non-covalently, or operatively coupled to the dephosphorylated LSD protein, to form a p97-agent conjugate. In some aspects, the p97 conjugate can be further coupled to one or more additional agents of interest, such as a small molecule and/or a detectable entity. Exemplary p97 polypeptide sequences and agents are described below. Also described are exemplary methods and components, such as linker groups, for coupling a p97 polypeptide to a dephosphorylated LSD protein or other agent of interest.

p97 Sequences.

In certain embodiments, a p97 polypeptide sequence used in a composition and/or conjugate of the invention comprises, consists essentially of, or consists of the human p97 sequence set forth in SEQ ID NO:1. Also included are variants and fragments thereof.

In some embodiments, a p97 polypeptide sequence comprises a sequence having at least 70%, 75%, 80%, 85%, 90%, 95%, 96%, 97%, 98%, or 99% identity or homology, along its length, to the human p97 sequence set forth in SEQ ID NO:1, or a portion thereof.

In particular embodiments, a p97 polypeptide sequence comprises a fragment of a human p97 sequence set forth in SEQ ID NO:1. In certain embodiments, a p97 polypeptide fragment is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730 or more amino acids in length, including all integers and ranges in between, and which may comprise all or a portion of the sequence of a reference p97 sequence such as SEQ ID NO:1.

In certain embodiments, a p97 polypeptide fragment is about 5-700, 5-600, 5-500, 5-400, 5-300, 5-200, 5-100, 5-50, 5-40, 5-30, 5-25, 5-20, 5-15, 5-10, 10-700, 10-600, 10-500, 10-400, 10-300, 10-200, 10-100, 10-50, 10-40, 10-30, 10-25, 10-20, 10-15, 20-700, 20-600, 20-500, 20-400, 20-300, 20-200, 20-100, 20-50, 20-40, 20-30, 20-25, 30-700, 30-600, 30-500, 30-400, 30-300, 30-200, 30-100, 30-50, 30-40, 40-700, 40-600, 40-500, 40-400, 40-300, 40-200, 40-100, 40-50, 50-700, 50-600, 50-500, 50-400, 50-300, 50-200, 50-100, 60-700, 60-600, 60-500, 60-400, 60-300, 60-200, 60-100, 60-70, 70-700, 70-600, 70-500, 70-400, 70-300, 70-200, 70-100, 70-80, 80-700, 80-600, 80-500, 80-400, 80-300, 80-200, 80-100, 80-90, 90-700, 90-600, 90-500, 90-400, 90-300, 90-200, 90-100, 100-700, 100-600, 100-500, 100-400, 100-300, 100-250, 100-200, 100-150, 200-700, 200-600, 200-500, 200-400, 200-300, or 200-250 amino acids in length, and comprises all or a portion of a reference p97 sequence such as SEQ ID NO:1.

In certain embodiments, p97 polypeptide sequences of interest include p97 amino acid sequences, subsequences, and/or variants of p97 that are effective for transporting an agent of interest across the blood brain barrier and into the central nervous system (CNS). In particular embodiments, the variant or fragment comprises the N-lobe of human p97 (residues 20-361 of SEQ ID NO:1). In specific aspects, the variant or fragment comprises an intact and functional $Fe^{3+}$-binding site.

In some embodiments, a p97 polypeptide sequence is a soluble form of a p97 polypeptide (see Yang et al., *Prot Exp Purif.* 34:28-48, 2004), or a fragment or variant thereof. In some aspects, the soluble p97 polypeptide has a deletion of the all or a portion of the hydrophobic domain (residues 710-738 of SEQ ID NO:1), alone or in combination with a deletion of all or a portion of the signal peptide (residues 1-19 of SEQ ID NO:1). In specific aspects, the soluble p97 polypeptide comprises or consists of residues 20-711 of SEQ ID NO:1, including variants and fragments thereof.

In certain embodiments, for instance, those that employ liposomes, the p97 polypeptide sequence is a lipid soluble form of a p97 polypeptide. For instance, certain of these and related embodiments include a p97 polypeptide that comprises all or a portion of the hydrophobic domain, optionally with or without the signal peptide.

In certain other embodiments, the p97 fragment or variant is capable of specifically binding to a p97 receptor, an LRP1 receptor and/or an LRP1B receptor.

Variants and fragments of reference p97 polypeptides and other reference polypeptides are described in greater detail below.

p97 Conjugates.

As noted above, certain embodiments comprise a p97 polypeptide that is linked to a dephosphorylated LSD protein or other agent of interest, for instance, a small molecule or a detectable entity, or any combination thereof. Also included are conjugates that comprise more than one dephosphorylated LSD protein and agent of interest, for instance, a p97 fragment conjugated to one or more dephosphorylated LSD proteins and a small molecule.

Covalent linkages are preferred, however, non-covalent linkages can also be employed, including those that utilize relatively strong non-covalent protein-ligand interactions, such as the interaction between biotin and avidin. Operative linkages are also included, which do not necessarily require a directly covalent or non-covalent interaction between the p97 polypeptide and the dephosphorylated LSD protein or agent of interest; examples of such linkages include liposome mixtures that comprise a p97 polypeptide and a dephosphorylated LSD protein and optionally an additional agent of interest. Exemplary methods of generating protein conjugates are described herein, and other methods are well-known in the art.

Small Molecules.

In particular embodiments, the p97 conjugate is further attached or linked to a small molecule. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than about 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

For the treatment of lysosomal storage disorders, exemplary classes of small molecules include those used for substrate reduction therapy and pharmacological chaperone therapy, premature nonsense mutation suppressors, and proteostasis regulators (see Smid et al., *Expert Opin. Investig. Drugs.* 19:1367-79, 2010; and Beck, *IUBMB Life.* 62:33-40, 2010).

In some aspects, the small molecule is an anti-inflammatory molecule. Examples include steroids and glucocorticoids (e.g., betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) such as aspirin, ibuprofen, naproxen, methotrexate, sulfasalazine, leflunomide, anti-TNF medications, cyclophosphamide and mycophenolate, among others.

Detectable Entities.

In some embodiments, the p97 conjugate is further attached or linked to a "detectable entity." Exemplary detectable entities include, without limitation, iodine-based labels, radioisotopes, fluorophores/fluorescent dyes, and nanoparticles.

Exemplary iodine-based labels include diatrizoic acid (Hypaque®, GE Healthcare) and its anionic form, diatrizoate. Diatrizoic acid is a radio-contrast agent used in advanced X-ray techniques such as CT scanning. Also included are iodine radioisotopes, described below.

Exemplary radioisotopes that can be used as detectable entities include $^{32}P$, $^{33}P$, $^{33}S$, $^{3}H$, $^{18}F$, $^{11}C$, $^{13}N$, $^{15}O$, $^{111}In$, $^{169}Yb$, $^{99m}TC$, $^{55}Fe$, and isotopes of iodine such as $^{123}I$, $^{124}I$, $^{125}I$, and $^{131}I$. These radioisotopes have different half-lives, types of decay, and levels of energy which can be tailored to match the needs of a particular protocol. Certain of these radioisotopes can be selectively targeted or better targeted to CNS tissues by conjugation to p97 polypeptides, for instance, to improve the medical imaging of such tissues.

Examples of fluorophores or fluorochromes that can be used as directly detectable entities include fluorescein, tetramethylrhodamine, Texas Red, Oregon Green®, and a number of others (e.g., Haugland, *Handbook of Fluorescent Probes*-9th Ed., 2002, Molec. Probes, Inc., Eugene Oreg.; Haugland, *The Handbook: A Guide to Fluorescent Probes and Labeling Technologies*-10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(c-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750. Certain embodiments include conjugation to chemotherapeutic agents (e.g., paclitaxel, adriamycin) that are labeled with a detectable entity, such as a fluorophore (e.g., Oregon Green®, Alexa Fluor 488).

Nanoparticles usually range from about 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots are fluorescing crystals about 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Polypeptide Variants and Fragments.

Certain embodiments include variants and/or fragments of the reference polypeptides described herein, whether described by name or by reference to a sequence identifier, including p97 polypeptides and LSD proteins. The wild-type or most prevalent sequences of these polypeptides are known in the art, and can be used as a comparison for the variants and fragments described herein.

A polypeptide "variant," as the term is used herein, is a polypeptide that typically differs from a polypeptide specifically disclosed herein by one or more substitutions, deletions, additions and/or insertions. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |

TABLE A -continued

| Amino Acids | | | Codons |
|---|---|---|---|
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In other specific embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing).

In still other specific embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution of about 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol. Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA*. 82: 488-492, 1985); Kunkel et al., (*Methods in Enzymol*. 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering*. 6: 327-331, 1993).

Exemplary Methods for Conjugation.

Conjugation or coupling of a p97 polypeptide sequence to lysosomal storage disorder (LSD) protein or other agent of interest can be carried out using standard chemical, biochemical and/or molecular techniques. Indeed, it will be apparent how to make a p97 conjugate in light of the present disclosure using available art-recognized methodologies. Of course, it will generally be preferred when coupling the primary components of a p97 conjugate of the present invention that the techniques employed and the resulting linking chemistries do not substantially disturb the desired functionality or activity of the individual components of the conjugate.

The particular coupling chemistry employed will depend upon the structure of the biologically active agent (e.g., small molecule, polypeptide), the potential presence of multiple functional groups within the biologically active agent, the need for protection/deprotection steps, chemical stability of the agent, and the like, and will be readily determined by one skilled in the art. Illustrative coupling chemistry useful for preparing the p97 conjugates of the invention can be found, for example, in Wong (1991), "Chemistry of Protein Conjugation and Crosslinking", CRC Press, Boca Raton, Fla.; and Brinkley "A Brief Survey of Methods for Preparing Protein Conjugates with Dyes, Haptens, and Crosslinking Reagents," in *Bioconjug. Chem.*, 3:2013, 1992. Preferably, the binding ability and/or activity of the conjugate is not substantially reduced as a result of the conjugation technique employed, for example, relative to the unconjugated LSD polypeptide or agent or the unconjugated p97 polypeptide.

In certain embodiments, a p97 polypeptide sequence may be coupled to a LSD polypeptide or other agent of interest either directly or indirectly. A direct reaction between a p97 polypeptide sequence and a LSD polypeptide or other agent of interest is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to indirectly couple a p97 polypeptide sequence and a LSD polypeptide or other agent of interest via a linker group, including non-peptide linkers and peptide linkers. A linker group can also function as a spacer to distance an agent of interest from the p97 polypeptide sequence in order to avoid interference with binding capabilities, targeting capabilities or other functionalities. A linker group can also serve to increase the chemical reactivity of a substituent on an agent, and thus increase the coupling efficiency. An increase in chemical reactivity may also facilitate the use of agents, or functional groups on agents, which otherwise would not be possible. The selection of releasable or stable linkers can also be employed to alter the pharmacokinetics of a p97 conjugate and attached antibody or other agent of interest. Illustrative linking groups include, for example, disulfide groups, thioether groups, acid labile groups, photolabile groups, peptidase labile groups and esterase labile groups. In other illustrative embodiments, the conjugates include linking groups such as those disclosed in U.S. Pat. No. 5,208,020 or EP Patent 0 425 235 B1, and Chari et al., Cancer Research. 52: 127-131, 1992. Additional exemplary linkers are described below.

In some embodiments, it may be desirable to couple more than one p97 polypeptide sequence to a LSD polypeptide or other agent, or vice versa. For example, in certain embodiments, multiple p97 polypeptide sequences are coupled to one LSD polypeptide or other agent, or alternatively, one or more p97 polypeptides are conjugated to multiple LSD polypeptides or other agents. The p97 polypeptide sequences can be the same or different. Regardless of the particular embodiment, conjugates containing multiple p97 polypeptide sequences may be prepared in a variety of ways. For example, more than one polypeptide may be coupled directly to an agent, or linkers that provide multiple sites for attachment can be used. Any of a variety of known heterobifunctional crosslinking strategies can be employed for making conjugates of the invention. It will be understood that many of these embodiments can be achieved by controlling the stoichiometries of the materials used during the conjugation/crosslinking procedure.

In certain exemplary embodiments, a reaction between an agent comprising a succinimidyl ester functional group and a p97 polypeptide comprising an amino group forms an amide linkage; a reaction between an agent comprising a oxycarbonylimidizaole functional group and a P97 polypeptide comprising an amino group forms an carbamate linkage; a reaction between an agent comprising a p-nitrophenyl carbonate functional group and a P97 polypeptide comprising an amino group forms an carbamate linkage; a reaction between an agent comprising a trichlorophenyl carbonate functional group and a P97 polypeptide comprising an amino group forms an carbamate linkage; a reaction between an agent comprising a thio ester functional group and a P97 polypeptide comprising an n-terminal amino group forms an amide linkage; a reaction between an agent comprising a proprionaldehyde functional group and a P97 polypeptide comprising an amino group forms a secondary amine linkage.

In some exemplary embodiments, a reaction between an agent comprising a butyraldehyde functional group and a P97 polypeptide comprising an amino group forms a secondary amine linkage; a reaction between an agent comprising an acetal functional group and a P97 polypeptide comprising an amino group forms a secondary amine linkage; a reaction between an agent comprising a piperidone functional group and a P97 polypeptide comprising an amino group forms a secondary amine linkage; a reaction between an agent comprising a methylketone functional group and a P97 polypeptide comprising an amino group forms a secondary amine linkage; a reaction between an agent comprising a tresylate functional group and a P97 polypeptide comprising an amino group forms a secondary amine linkage; a reaction between an agent comprising a maleimide functional group and a P97 polypeptide comprising an amino group forms a secondary amine linkage; a reaction between an agent comprising a aldehyde functional group and a P97 polypeptide comprising an amino group forms a secondary amine linkage; and a reaction between an agent comprising a hydrazine functional group and a P97 polypeptide comprising an carboxylic acid group forms a secondary amine linkage.

In particular exemplary embodiments, a reaction between an agent comprising a maleimide functional group and a P97 polypeptide comprising a thiol group forms a thio ether linkage; a reaction between an agent comprising a vinyl sulfone functional group and a P97 polypeptide comprising a thiol group forms a thio ether linkage; a reaction between an agent comprising a thiol functional group and a P97 polypeptide comprising a thiol group forms a di-sulfide linkage; a reaction between an agent comprising a orthopyridyl disulfide functional group and a P97 polypeptide comprising a thiol group forms a di-sulfide linkage; and a reaction between an agent comprising an iodoacetamide functional group and a P97 polypeptide comprising a thiol group forms a thio ether linkage.

In a specific embodiment, an amine-to-sulfhydryl cross-linker is used for preparing a conjugate. In one preferred embodiment, for example, the crosslinker is succinimidyl-4-(N-maleimidomethyl)cyclohexane-1-carboxylate (SMCC) (Thermo Scientific), which is a sulfhydryl crosslinker containing NHS-ester and maleimide reactive groups at opposite ends of a medium-length cyclohexane-stabilized spacer arm (8.3 angstroms). SMCC is a non-cleavable and membrane permeable crosslinker that can be used to create sulfhydryl-reactive, maleimide-activated agents (e.g., polypeptides, antibodies) for subsequent reaction with p97 polypeptide sequences. NHS esters react with primary amines at pH 7-9 to form stable amide bonds. Maleimides react with sulfhydryl groups at pH 6.5-7.5 to form stable thioether bonds. Thus, the amine reactive NHS ester of SMCC crosslinks rapidly with primary amines of an agent and the resulting sulfhydryl-reactive maleimide group is then available to react with cysteine residues of p97 to yield specific conjugates of interest.

In certain specific embodiments, the p97 polypeptide sequence is modified to contain exposed sulfhydryl groups to facilitate crosslinking, e.g., to facilitate crosslinking to a maleimide-activated agent. In a more specific embodiment, the p97 polypeptide sequence is modified with a reagent which modifies primary amines to add protected thiolsulfhydryl groups. In an even more specific embodiment, the reagent N-succinimidyl-5-acetylthioacetate (SATA) (Thermo Scientific) is used to produce thiolated p97 polypeptides.

In other specific embodiments, a maleimide-activated agent is reacted under suitable conditions with thiolated p97 polypeptides to produce a conjugate of the present invention. It will be understood that by manipulating the ratios of SMCC, SATA, agent, and p97 polypeptide in these reactions it is possible to produce conjugates having differing stoichiometries, molecular weights and properties.

In still other illustrative embodiments, conjugates are made using bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage.

The specific crosslinking strategies discussed herein are but a few of many examples of suitable conjugation strategies that may be employed in producing conjugates of the invention. It will be evident to those skilled in the art that a variety of other bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Particular embodiments may employ one or more aldehyde tags to facilitate conjugation between a p97 polypeptide and a LSD polypeptide or other agent (see U.S. Pat. Nos. 8,097,701 and 7,985,783, incorporated by reference). Here, enzymatic modification at a sulfatase motif of the aldehyde tag through action of a formylglycine generating enzyme (FGE) generates a formylglycine (FGly) residue. The aldehyde moiety of the FGly residue can then be exploited as a chemical handle for site-specific attachment of a moiety of interest to the polypeptide. In some aspects, the moiety of interest is a small molecule, peptoid, aptamer, or peptide mimetic. In some aspects, the moiety of interest is another polypeptide, such as an antibody.

Particular embodiments thus include a p97 polypeptide or LSD polypeptide or other polypeptide agent that comprises 1, 2, 3, 4, 5, 6, 7, 8, 9, 10 or more heterologous sulfatase motifs, where the motif comprises the following structure:

(SEQ ID NO: 4)
$X_1Z_1X_2Z_2X_3$ where $Z_1$ is cysteine or serine; $Z_2$ is a proline or alanine residue; $X_1$ is present or absent and, when present, is any amino acid, where $X_1$ is preferably present when the heterologous sulfatase motif is at an N-terminus of the aldehyde tagged polypeptide; and $X_2$ and $X_3$ are each independently any amino acid.

Polypeptides with the above-described motif can be modified by an FGE enzyme to generate a motif having a FGly residue, which, as noted above, can then be used for site-specific attachment of an agent, such as a second polypeptide, for instance, via a linker moiety. Such modifications can be performed, for example, by expressing the sulfatase motif-containing polypeptide (e.g., p97, LSD polypeptide) in a mammalian, yeast, or bacterial cell that expresses an FGE enzyme or by in vitro modification of isolated polypeptide with an isolated FGE enzyme (see Wu et al., *PNAS*. 106:3000-3005, 2009; Rush and Bertozzi, *J. Am. Chem. Soc.* 130:12240-1, 2008; and Carlson et al., *J Biol. Chem.* 283: 20117-25, 2008).

Hence, some embodiments include a p97 polypeptide or polypeptide agent (e.g., LSD polypeptide) that comprises 1, 2, 3, 4, 5, 6, 7, 8, 9, 10 or more heterologous sulfatase motifs having a formylglycine residue, where the motif comprises the following structure:

$$X_1(FGly)X_2Z_2X_3 \quad (SEQ\ ID\ NO: 5)$$

where FGly is a formylglycine residue; $Z_2$ is a proline or alanine residue; $X_1$ is present or absent and, when present, is any amino acid, where $X_1$ is preferably present when the heterologous sulfatase motif is at an N-terminus of the aldehyde tagged polypeptide; and $X_2$ and $X_3$ are each independently any amino acid.

In particular embodiments, $X_1$, $X_2$, and $X_3$ are each independently an aliphatic amino acid, a sulfur-containing amino acid or a polar, uncharged amino acid. For instance, $X_1$ can be L, M, V, S or T; and $X_2$, and/or $X_3$ can be independently S, T, A, V, G or C.

In some embodiments, the heterologous sulfatase motif(s) can be (a) less than 16 amino acid residues in length, including about 4, 5, 6, 7, 8, 9, 10, 11, 12, 13, 14, or 15 residues in length, (b) positioned at the N-terminus of the polypeptide, (c) positioned at the C-terminus of the polypeptide, (d) positioned at an internal site of an amino acid sequence native to the polypeptide, (e) positioned in a terminal loop of the polypeptide, (f) positioned at a site of post-translational modification of the polypeptide (e.g., glycosylation site), or any combination thereof.

Some embodiments relate to conjugates of (i) a sulfatase motif (or aldehyde tag)-containing p97 polypeptide, and (ii) an agent (A) such as small molecule that is functionalized with an aldehyde reactive group, where (i) and (ii) are covalently linked via the FGly residue of the sulfatase motif and the aldehyde reactive group. Such conjugates can have one of the following general structures:

p97(FGly)-$R_1$-A where $R_1$ is at least one aldehyde reactive linkage; and FGly is a formylglycine residue within a heterologous sulfatase motif.

Some embodiments relate to conjugates of (i) a sulfatase motif (or aldehyde tag)-containing p97 polypeptide, and (ii) a polypeptide agent (pA) that is functionalized with an aldehyde reactive group, or vice versa, where (i) and (ii) are covalently linked via the FGly residue of the sulfatase motif and the aldehyde reactive group. Such conjugates can have one of the following general structures:

p97(FGly)-$R_1$-pA or p97-$R_1$-(FGly)pA where $R_1$ is at least one aldehyde reactive linkage; and FGly is a formylglycine residue within a heterologous sulfatase motif.

The agent or non-aldehyde tag-containing polypeptide (e.g., p97 polypeptide, LSD polypeptide) can be functionalized with one or more aldehyde reactive groups such as aminooxy, hydrazide, and thiosemicarbazide, and then covalently linked to the aldehyde tag-containing polypeptide via the at least one FGly residue, to form an aldehyde reactive linkage. The attachment of an aminooxy functionalized agent (or non-aldehyde tag-containing polypeptide) creates an oxime linkage between the FGly residue and the functionalized agent (or non-aldehyde tag-containing polypeptide); attachment of a hydrazide-functionalized agent (or non-aldehyde tag-containing polypeptide) creates a hydrazine linkage between the FGly residue and the functionalized agent (or non-aldehyde tag-containing polypeptide); and attachment of a thiosemicarbazide-functionalized agent (or non-aldehyde tag-containing polypeptide) creates a hydrazine carbothiamide linkage between the FGly residue and the functionalized agent (or non-aldehyde tag-containing polypeptide). Hence, in these and related embodiments, $R_1$ can be a linkage that comprises a Schiff base, such as an oxime linkage, a hydrazine linkage, or a hydrazine carbothiamide linkage.

Certain embodiments include conjugates of (i) a sulfatase motif (or aldehyde tag)-containing p97 polypeptide and (ii) a sulfatase motif (or aldehyde tag)-containing LSD polypeptide agent (A), where (i) and (ii) are covalently linked via their respective FGly residues, optionally via a bi-functionalized linker moiety or group. For instance, certain p97 conjugates may comprise the following structure:

p97(FGly)-$R_1$-L-$R_2$-(FGly)A where $R_1$ and $R_2$ are the same or different aldehyde reactive linkage; L is a linker moiety, p97(FGly) is a aldehyde-tag containing p97 polypeptide, and (FGly)A is an aldehyde tag-containing agent, such as an LSD polypeptide agent.

Merely by way of illustration, in some embodiments, the at least one heterologous sulfatase motif can be at the C-terminus of the p97 polypeptide and the N-terminus of the polypeptide-based agent (e.g., LSD polypeptide). In other embodiments, the at least one heterologous sulfatase motif can be at the N-terminus of the p97 polypeptide and the C-terminus of the polypeptide-based agent. In still other embodiments, the at least one heterologous sulfatase motif can be at the N-terminus of the p97 polypeptide and the N-terminus of the polypeptide-based agent. In further embodiments, the at least one heterologous sulfatase motif can be at the C-terminus of the p97 polypeptide an the C-terminus of the polypeptide-based agent. As noted above, the at least one heterologous motif can be at an internal position in the p97 polypeptide and/or the polypeptide-based agent. Persons skilled in the art will recognize that other combinations are possible.

The aldehyde reactive linkages of $R_1$ and $R_2$ can be independently formed by any aldehyde reactive group that will form a covalent bond between (i) the formylglycine (FGly) residue of the aldehyde tag and (ii) a linker moiety that is functionalized with said aldehyde reactive group (e.g., a bi-functionalized linker with two aldehyde reactive groups, which can be the same or different). Examples of aldehyde reactive groups include aminooxy, hydrazide, and thiosemicarbazide groups, which will form Schiff-base containing linkages with a FGly residue, including oxime linkages, hydrazine linkages, and hydrazine carbothiamide linkages, respectively. Hence, $R_1$ and $R_2$ can be independently a linkage that comprises a Schiff base, such as an oxime linkage, a hydrazine linkage, or a hydrazine carbothiamide linkage.

In some embodiments, the aldehyde tag-containing p97 polypeptide and the aldehyde tag-containing LSD polypeptide or other agent are linked (e.g., covalently linked) via a multi-functionalized linker (e.g., bi-functionalized linker), the latter being functionalized with the same or different aldehyde reactive group(s). In these and related embodiments, the aldehyde reactive groups allow the linker to form a covalent bridge between the p97 polypeptide and the LSD polypeptide or other agent via their respective FGly residues. Linker moieties include any moiety or chemical that can be functionalized and preferably bi- or multi-functionalized with one or more aldehyde reactive groups. Particular examples include peptides, water-soluble polymers, detectable entities, other therapeutic compounds (e.g., cytotoxic compounds), biotin/streptavidin moieties, and glycans (see Hudak et al., *J Am Chem. Soc.* 133:16127-35, 2011). Specific examples of glycans (or glycosides) include aminooxy glycans, such as higher-order glycans composed of glycosyl N-pentenoyl hydroxamates intermediates (supra). Exemplary linkers are described herein, and can be functionalized with aldehyde reactive groups according to routine techniques in the art (see, e.g., Carrico et al., *Nat Chem. Biol.* 3:321-322, 2007; and U.S. Pat. Nos. 8,097,701 and 7,985,783).

p97 conjugates can also be prepared by a various "click chemistry" techniques, including reactions that are modular, wide in scope, give very high yields, generate mainly inoffensive byproducts that can be removed by non-chromatographic methods, and can be stereospecific but not necessarily enantioselective (see Kolb et al., *Angew Chem Int Ed Engl.* 40:2004-2021, 2001). Particular examples include conjugation techniques that employ the Huisgen 1,3-dipolar cycloaddition of azides and alkynes, also referred to as "azide-alkyne cycloaddition" reactions (see Hein et al., *Pharm Res.* 25:2216-2230, 2008). Non-limiting examples of azide-alkyne cycloaddition reactions include copper-catalyzed azide-alkyne cycloaddition (CuAAC) reactions and ruthenium-catalyzed azide-alkyne cycloaddition (RuAAC) reactions.

CuAAC works over a broad temperature range, is insensitive to aqueous conditions and a pH range over 4 to 12, and tolerates a broad range of functional groups (see Himo et al, *J Am Chem. Soc.* 127:210-216, 2005). The active Cu(I) catalyst can be generated, for example, from Cu(I) salts or Cu(II) salts using sodium ascorbate as the reducing agent. This reaction forms 1,4-substituted products, making it region-specific (see Hein et al., supra).

RuAAC utilizes pentamethylcyclopentadienyl ruthenium chloride [Cp*RuCl] complexes that are able to catalyze the cycloaddition of azides to terminal alkynes, regioselectively leading to 1,5-disubstituted 1,2,3-triazoles (see Rasmussen et al., *Org. Lett.* 9:5337-5339, 2007). Further, and in contrast to CuAAC, RuAAC can also be used with internal alkynes to provide fully substituted 1,2,3-triazoles.

Certain embodiments thus include p97 polypeptides that comprise at least one unnatural amino acid with an azide side-chain or an alkyne side-chain, including internal and terminal unnatural amino acids (e.g., N-terminal, C-terminal). Certain of these p97 polypeptides can be formed by in vivo or in vitro (e.g., cell-free systems) incorporation of unnatural amino acids that contain azide side-chains or alkyne side-chains. Exemplary in vivo techniques include cell culture techniques, for instance, using modified *E. coli* (see Travis and Schultz, *The Journal of Biological Chemistry.* 285:11039-44, 2010; and Deiters and Schultz, *Bioorganic & Medicinal Chemistry Letters.* 15:1521-1524, 2005), and exemplary in vitro techniques include cell-free systems (see Bundy, *Bioconjug Chem.* 21:255-63, 2010).

In some embodiments, a p97 polypeptide that comprises at least one unnatural amino acid with an azide side-chain is conjugated by azide-alkyne cycloaddition to an agent (or linker) that comprises at least one alkyne group, such as an antibody or other polypeptide agent that comprises at least one unnatural amino acid with an alkyne side-chain. In other embodiments, a p97 polypeptide that comprises at least one unnatural amino acid with an alkyne side-chain is conjugated by azide-alkyne cycloaddition to an antibody or other polypeptide agent (or linker) that comprises at least one azide group, such as a polypeptide agent that comprises at least one unnatural amino acid with an azide side-chain. Hence, certain embodiments include conjugates that comprise a p97 polypeptide covalently linked to an agent via a 1,2,3-triazole linkage.

Specific p97 conjugates can be formed by the following CuAAC-based or RuAAC-based reactions, to comprise the following respective structures (I) or (II).

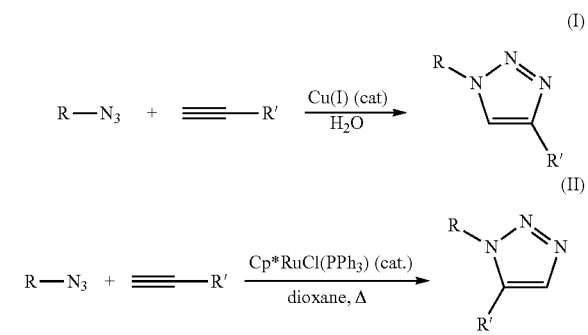

where R is a p97 polypeptide and R$^I$ is an agent of interest (or linker); or where R is an agent of interest (or linker) and R$^I$ is a p97 polypeptide.

In certain embodiments, the unnatural amino acid with the azide side-chain and/or the unnatural amino acid with alkyne side-chain are terminal amino acids (N-terminal, C-terminal). In certain embodiments, one or more of the unnatural amino acids are internal.

For instance, certain embodiments include a p97 polypeptide that comprises an N-terminal unnatural amino acid with an azide side-chain conjugated to an agent that comprises an alkyne group. Some embodiments, include a p97 polypeptide that comprises a C-terminal unnatural amino acid with an azide side-chain conjugated to an agent that comprises an alkyne group. Particular embodiments include a p97 polypeptide that comprises an N-terminal unnatural amino acid with an alkyne side-chain conjugated to an agent that comprises an azide side-group. Further embodiments include a p97 polypeptide that comprises an C-terminal unnatural amino acid with an alkyne side-chain conjugated to an agent that comprises an azide side-group. Some embodiments include a p97 polypeptide that comprises at least one internal unnatural amino acid with an azide side-chain conjugated to an agent that comprises an alkyne group. Additional embodiments include a p97 polypeptide that comprises at least one internal unnatural amino acid with an alkyne side-chain conjugated to an agent that comprises an azide side-group Particular embodiments include a p97 polypeptide that comprises an N-terminal unnatural amino acid with an azide side-chain conjugated to a polypeptide agent that comprises an N-terminal unnatural amino acid with an alkyne side-chain. Other embodiments include a p97 polypeptide that comprises a C-terminal unnatural amino acid with an azide side-chain conjugated to a polypeptide agent that comprises a C-terminal unnatural amino acid with an alkyne side-chain. Still other embodiments include a p97 polypeptide that comprises an N-terminal unnatural amino acid with an azide side-chain conjugated to a polypeptide agent that comprises a C-terminal unnatural amino acid with an alkyne side-chain. Further embodiments include a p97 polypeptide that comprises a C-terminal unnatural amino acid with an azide side-chain conjugated to a polypeptide agent that comprises an N-terminal unnatural amino acid with an alkyne side-chain.

Other embodiments include a p97 polypeptide that comprises an N-terminal unnatural amino acid with an alkyne side-chain conjugated to a polypeptide agent that comprises an N-terminal unnatural amino acid with an azide side-chain. Still further embodiments include a p97 polypeptide that comprises a C-terminal unnatural amino acid with an alkyne side-chain conjugated to a polypeptide agent that comprises a C-terminal unnatural amino acid with an azide side-chain. Additional embodiments include a p97 polypeptide that comprises an N-terminal unnatural amino acid with an alkyne side-chain conjugated to a polypeptide agent that comprises a C-terminal unnatural amino acid with an azide side-chain. Still further embodiments include a p97 polypeptide that comprises a C-terminal unnatural amino acid with an alkyne side-chain conjugated to a polypeptide agent that comprises an N-terminal unnatural amino acid with an azide side-chain.

Also included are methods of producing a p97 conjugate, comprising: (a) performing an azide-alkyne cycloaddition reaction between (i) a p97 polypeptide that comprises at least one unnatural amino acid with an azide side-chain and an agent that comprises at least one alkyne group (for instance, an unnatural amino acid with an alkyne side chain); or (ii) a p97 polypeptide that comprises at least one unnatural amino acid with an alkyne side-chain and an agent that comprises at least one azide group (for instance, an unnatural amino acid with an azide side-chain); and (b) isolating a p97 conjugate from the reaction, thereby producing a p97 conjugate.

In the case where the p97 conjugate is a fusion polypeptide, the fusion polypeptide may generally be prepared using standard techniques. Preferably, however, a fusion polypeptide is expressed as a recombinant polypeptide in an expression system, described herein and known in the art. Fusion polypeptides of the invention can contain one or multiple copies of a p97 polypeptide sequence and may contain one or multiple copies of a polypeptide-based agent of interest (e.g., LSD polypeptide), present in any desired arrangement.

For fusion proteins, DNA sequences encoding the p97 polypeptide, the polypeptide agent (e.g., LSD polypeptide), and optionally peptide linker components may be assembled separately, and then ligated into an appropriate expression vector. The 3' end of the DNA sequence encoding one polypeptide component is ligated, with or without a peptide linker, to the 5' end of a DNA sequence encoding the other polypeptide component(s) so that the reading frames of the sequences are in phase.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the most C-terminal polypeptide. This permits translation into a single fusion polypeptide that retains the biological activity of both component polypeptides.

Similar techniques, mainly the arrangement of regulatory elements such as promoters, stop codons, and transcription termination signals, can be applied to the recombinant production of non-fusion proteins, for instance, p97 polypeptides and polypeptide agents (e.g., antibody agents) for the production of non-fusion conjugates.

Polynucleotides and fusion polynucleotides of the invention can contain one or multiple copies of a nucleic acid encoding a p97 polypeptide sequence, and/or may contain one or multiple copies of a nucleic acid encoding a polypeptide agent such as a LSD polypeptide.

In some embodiments, a nucleic acids encoding a subject p97 polypeptide, antibody or other polypeptide agent, and/or p97-polypeptide fusion are introduced directly into a host cell, and the cell incubated under conditions sufficient to induce expression of the encoded polypeptide(s). The polypeptide sequences of this disclosure may be prepared using standard techniques well known to those of skill in the art in combination with the polypeptide and nucleic acid sequences provided herein.

Therefore, according to certain related embodiments, there is provided a recombinant host cell which comprises a polynucleotide or a fusion polynucleotide that encodes a polypeptide described herein. Expression of a p97 polypeptide, LSD polypeptide, or p97-LSD polypeptide fusion in the host cell may conveniently be achieved by culturing under appropriate conditions recombinant host cells containing the polynucleotide. Following production by expression, the polypeptide(s) may be isolated and/or purified using any suitable technique, and then used as desired.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary (CHO) cells, HeLa cells, baby hamster kidney cells, HEK-293 cells, NSO mouse melanoma cells and many others. A common, preferred bacterial host is *E. coli*. The expression of polypeptides in prokaryotic cells such as *E. coli* is well established in the art. For a review, see for example Pluckthun, A. *Bio/Technology*. 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the polypeptides described herein, and which further expresses or is capable of expressing a selected gene of interest, such as a gene encoding any herein described polypeptide. The term includes the progeny of the parent cell, whether or not the progeny are identical in morphology or in genetic make-up to the original parent, so long as the selected gene is present. Host cells may be chosen for certain characteristics, for instance, the expression of a formylglycine generating enzyme (FGE) to convert a cysteine or serine residue within a sulfatase motif into a formylglycine (FGly) residue, or the expression of aminoacyl tRNA synthetase(s) that can incorporate unnatural amino acids into the polypeptide, including unnatural amino acids with an azide side-chain, alkyne side-chain, or other desired side-chain, to facilitate conjugation.

Accordingly there is also contemplated a method comprising introducing such nucleic acid(s) into a host cell. The introduction of nucleic acids may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene. In one embodiment, the nucleic acid is integrated into the genome (e.g. chromosome) of the host cell. Integration may be promoted by inclusion of sequences which promote recombination with the genome, in accordance with standard techniques.

The present invention also provides, in certain embodiments, a method which comprises using a nucleic acid construct described herein in an expression system in order to express a particular polypeptide, such as a p97 polypeptide, LSD polypeptide, or p97-LSD polypeptide fusion protein as described herein.

As noted above, certain p97 conjugates, such as fusion proteins, may employ one or more linker groups, including non-peptide linkers (e.g., non-proteinaceous linkers) and peptide linkers. Such linkers can be stable linkers or releasable linkers.

Exemplary non-peptide stable linkages include succinimide, propionic acid, carboxymethylate linkages, ethers, carbamates, amides, amines, carbamides, imides, aliphatic C—C bonds, thio ether linkages, thiocarbamates, thiocarbamides, and the like. Generally, a hydrolytically stable linkage is one that exhibits a rate of hydrolysis of less than about 1-2% to 5% per day under physiological conditions.

Exemplary non-peptide releasable linkages include carboxylate ester, phosphate ester, anhydride, acetal, ketal, acyloxyalkyl ether, imine, orthoester, thio ester, thiol ester, carbonate, and hydrazone linkages. Additional illustrative embodiments of hydrolytically unstable or weak linkages include, but are not limited to: $-O_2C-(CH_2)_b-O-$, where b is from 1 to 5, $-O-(CH_2)_b-CO_2-(CH_2)_c-$, where b is from 1 to 5 and c is from 2-5, $-O-(CH_2)_b-CO_2-(CH_2)_c-O-$, where b is from 1 to 5 and c is from 2-5, $-(CH_2)_b-OPO_3-(CH_2)_{b'}-$, where b is 1-5 and b' is 1-5, $-C(O)-(NH-CHR-CO)_a-NH-CHR-$, where a is 2 to 20 and R is a substituent found on an α-amino acid, $-O-(CH_2)_b-CO_2-CHCH_2-CH_2-$, where b is from 1-5, $-O-C_6H_4-CH=N-(CH_2)_b-O-$, where b is from 1-5, and $-O-(CH_2)_b-CH_2-CH=N-(CH_2)_b-O-$, where each b is independently from 1-5.

Other illustrative examples of releasable linkers can be benzyl elimination-based linkers, trialkyl lock-based linkers (or trialkyl lock lactonization based), bicine-based linkers, and acid labile linkers. Among the acid labile linkers can be disulfide bond, hydrazone-containing linkers and thiopropionate-containing linkers.

Also included are linkers that are releasable or cleavable during or upon internalization into a cell. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.). In one embodiment, an acid-labile linker may be used (Cancer Research 52:127-131, 1992; and U.S. Pat. No. 5,208,020).

In certain embodiments, "water soluble polymers" are used in a linker for coupling a p97 polypeptide sequence to an agent of interest. A "water-soluble polymer" refers to a polymer that is soluble in water and is usually substantially non-immunogenic, and usually has an atomic molecular weight greater than about 1,000 Daltons. Attachment of two polypeptides via a water-soluble polymer can be desirable as such modification(s) can increase the therapeutic index by increasing serum half-life, for instance, by increasing proteolytic stability and/or decreasing renal clearance. Additionally, attachment via of one or more polymers can reduce the immunogenicity of protein pharmaceuticals. Particular examples of water soluble polymers include polyethylene glycol, polypropylene glycol, polyoxyalkylenes, or copolymers of polyethylene glycol, polypropylene glycol, and the like.

In some embodiments, the water-soluble polymer has an effective hydrodynamic molecular weight of greater than about 10,000 Da, greater than about 20,000 to 500,000 Da, greater than about 40,000 Da to 300,000 Da, greater than about 50,000 Da to 70,000 Da, usually greater than about 60,000 Da. The "effective hydrodynamic molecular weight" refers to the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of between about 200 Da and about 80,000 Da, or between about 1,500 Da and about 42,000 Da, with 2,000 to about 20,000 Da being of particular interest. Linear, branched, and terminally charged water soluble polymers are also included.

Polymers useful as linkers between aldehyde tagged polypeptides can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol (PEG), methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically described water-soluble polymers are also included.

Water-soluble polymers are known in the art, particularly the polyalkylene oxide-based polymers such as polyethylene glycol "PEG" (see Poly(ethylene glycol) Chemistry: Biotechnical and Biomedical Applications, J. M. Harris, Ed., Plenum Press, New York, N.Y. (1992); and Poly(ethylene glycol) Chemistry and Biological Applications, J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966, incorporated by reference).

Exemplary polymers of interest include those containing a polyalkylene oxide, polyamide alkylene oxide, or derivatives thereof, including polyalkylene oxide and polyamide alkylene oxide comprising an ethylene oxide repeat unit of the formula $—(CH_2—CH^2—O)—$. Further exemplary polymers of interest include a polyamide having a molecular weight greater than about 1,000 Daltons of the formula $—[C(O)—X—C(O)—NH—Y—NH]_n—$ or $—[NH—Y—NH—C(O)—X—C(O)]_n—$, where X and Y are divalent radicals that may be the same or different and may be branched or linear, and n is a discrete integer from 2-100, usually from 2 to 50, and where either or both of X and Y comprises a biocompatible, substantially non-antigenic water-soluble repeat unit that may be linear or branched.

Further exemplary water-soluble repeat units comprise an ethylene oxide of the formula $—(CH_2—CH_2—O)—$ or $—(CH_2—CH_2—O)—$. The number of such water-soluble repeat units can vary significantly, with the usual number of such units being from 2 to 500, 2 to 400, 2 to 300, 2 to 200, 2 to 100, and most usually 2 to 50. An exemplary embodiment is one in which one or both of X and Y is selected from: $—((CH_2)_{n1}—(CH_2—CH_2—O)_{n2}—(CH_2)—$ or $—((CH_2)_{n1}—(O—CH_2—CH_2)_{n2}—(CH_2)_{n1}—)$, where n1 is 1 to 6, 1 to 5, 1 to 4 and most usually 1 to 3, and where n2 is 2 to 50, 2 to 25, 2 to 15, 2 to 10, 2 to 8, and most usually 2 to 5. A further exemplary embodiment is one in which X is $—(CH_2—CH_2)—$, and where Y is $—(CH_2—(CH_2—CH_2—O)_3—CH_2—CH_2—CH_2)—$ or $—(CH_2—CH_2—CH_2—(O—CH_2—CH_2)_3—CH_2)—$, among other variations.

In certain embodiments, a peptide linker sequence may be employed to separate or couple the components of a p97 conjugate. For instance, for polypeptide-polypeptide conjugates, peptide linkers can separate the components by a distance sufficient to ensure that each polypeptide folds into its secondary and tertiary structures. Such a peptide linker sequence may be incorporated into the conjugate (e.g., fusion protein) using standard techniques described herein and well-known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180.

In certain illustrative embodiments, a peptide linker is between about 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide linker comprises about 1, 5, 10, 15, 20, 25, 30, 35, 40, 45, 50 or more amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., *Gene* 40:39-46, 1985; Murphy et al., *PNAS USA.* 83:8258-8262, 1986; U.S. Pat. No. 4,935,233 and U.S. Pat. No. 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: $[G]_x$, $[S]_x$, $[N]_x$, $[GS]_x$, $[GGS]_x$, $[GSS]_x$, $[GSGS]_x$ (SEQ ID NO:6), $[GGSG]_x$ (SEQ ID NO: 7), $[GGGS]_x$ (SEQ ID NO:8), $[GGGGS]_x$ (SEQ ID NO:9), $[GN]_x$, $[GGN]_x$, $[GNN]_x$, $[GNGN]_x$ (SEQ ID NO:10), $[GGNG]_x$ (SEQ ID NO:11), $[GGGN]_x$ (SEQ ID NO:12), $[GGGGN]_x$ (SEQ ID NO:13) linkers, where $_x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art.

In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, *PNAS.* 90:2256-2260, 1993; and *PNAS.* 91:11099-11103, 1994) or by phage display methods.

The peptide linkers may be physiologically stable or may include a releasable linker such as a physiologically degradable or enzymatically degradable linker (e.g., proteolytically cleavable linker). In certain embodiments, one or more releasable linkers can result in a shorter half-life and more rapid clearance of the conjugate. These and related embodiments can be used, for example, to enhance the solubility and blood circulation lifetime of p97 conjugates in the bloodstream, while also delivering an agent into the bloodstream (or across the BBB) that, subsequent to linker degradation, is substantially free of the p97 sequence. These aspects are especially useful in those cases where polypeptides or other agents, when permanently conjugated to a p97 sequence, demonstrate reduced activity. By using the linkers as provided herein, such antibodies can maintain their therapeutic activity when in conjugated form. In these and other ways, the properties of the p97 conjugates can be more effectively tailored to balance the bioactivity and circulating half-life of the antibodies over time.

Enzymatically degradable linkages suitable for use in particular embodiments of the present invention include, but are not limited to: an amino acid sequence cleaved by a serine protease such as thrombin, chymotrypsin, trypsin, elastase, kallikrein, or substilisin. Illustrative examples of thrombin-cleavable amino acid sequences include, but are not limited to: -Gly-Arg-Gly-Asp- (SEQ ID NO:14), -Gly-Gly-Arg-, -Gly-Arg-Gly-Asp-Asn-Pro- (SEQ ID NO:15), -Gly-Arg-Gly-Asp-Ser- (SEQ ID NO:16), -Gly-Arg-Gly-Asp-Ser-Pro-Lys- (SEQ ID NO:17), -Gly-Pro-Arg-, -Val-Pro-Arg-, and -Phe-Val-Arg-. Illustrative examples of elastase-cleavable amino acid sequences include, but are not limited to: -Ala-Ala-Ala-, -Ala-Ala-Pro-Val- (SEQ ID NO:18), -Ala-Ala-Pro-Leu- (SEQ ID NO:19), -Ala-Ala-Pro-Phe- (SEQ ID NO:20), -Ala-Ala-Pro-Ala- (SEQ ID NO:21), and -Ala-Tyr-Leu-Val- (SEQ ID NO:22).

Enzymatically degradable linkages suitable for use in particular embodiments of the present invention also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z- (SEQ ID NO:23), -Gly-Pro-, Leu-Gly-Pro-Z- (SEQ ID NO:24), -Gly-Pro-Ile-Gly-Pro-Z- (SEQ ID NO:25), and -Ala-Pro-Gly-Leu-Z- (SEQ ID NO: 26), where Y and Z are amino acids. Illustrative examples of collagenase-cleavable amino acid sequences include, but are not limited to: -Pro-Leu-Gly-Pro-D-Arg-Z- (SEQ ID NO:27), -Pro-Leu-Gly-Leu-Leu-Gly-Z- (SEQ ID NO:28), -Pro-Gln-Gly-Ile-Ala-Gly-Trp- (SEQ ID NO:29), -Pro-Leu-Gly-Cys(Me)-His- (SEQ ID NO:30), -Pro-Leu-Gly-Leu-Tyr-Ala- (SEQ ID NO:31), -Pro-Leu-Ala-Leu-Trp-Ala-Arg- (SEQ ID NO:32), and -Pro-Leu-Ala-Tyr-Trp-Ala-Arg- (SEQ ID NO:33), where Z is an amino acid. An illustrative example of a stromelysin-cleavable amino acid sequence is -Pro-Tyr-Ala-Tyr-Tyr-Met-Arg- (SEQ ID NO:34); and an example of a gelatinase-cleavable amino acid sequence is -Pro-Leu-Gly-Met-Tyr-Ser-Arg- (SEQ ID NO:35).

Enzymatically degradable linkages suitable for use in particular embodiments of the present invention also include amino acid sequences that can be cleaved by an angiotensin converting enzyme, such as, for example, -Asp-Lys-Pro-, -Gly-Asp-Lys-Pro- (SEQ ID NO:36), and -Gly-Ser-Asp-Lys-Pro- (SEQ ID NO:37).

Enzymatically degradable linkages suitable for use in particular embodiments of the present invention also include amino acid sequences that can be degraded by cathepsin B, such as, for example, -Val-Cit-, -Ala-Leu-Ala-Leu- (SEQ ID NO:38), -Gly-Phe-Leu-Gly- (SEQ ID NO:39) and -Phe-Lys-.

In certain embodiments, however, any one or more of the non-peptide or peptide linkers are optional. For instance, linker sequences may not required in a fusion protein where the first and second polypeptides have non-essential N-terminal and/or C-terminal amino acid regions that can be used to separate the functional domains and prevent steric interference.

The functional properties of the p97 polypeptides and p97 polypeptide conjugates described herein may be assessed using a variety of methods known to the skilled person, including, e.g., affinity/binding assays (for example, surface plasmon resonance, competitive inhibition assays). For instance, the conjugates described herein may be tested for effects on receptor internalization, in vitro and in vivo efficacy, etc., including the rate of transport across the blood brain barrier. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

Methods of Use and Pharmaceutical Compositions

Certain embodiments of the present invention relate to methods of using the compositions of dephosphorylated lysosomal storage disorder (LSD) proteins and related p97 conjugates described herein. Examples of such methods include methods of treatment and methods of diagnosis, including for instance, the use of dephosphorylated LSD proteins or related p97 conjugates for medical imaging of certain organs/tissues, such as those of the nervous system. Some embodiments include methods of diagnosing and/or treating disorders or conditions of the central nervous system (CNS), or disorders or conditions having a CNS component. Particular aspects include methods of treating a lysosomal storage disorder (LSD), including those having a CNS component.

Accordingly, certain embodiments include methods of treating a subject in need thereof, comprising administering a composition that comprises a substantially dephosphorylated LSD protein described herein, or p97 conjugate thereof. Also included are methods of delivering an agent to the nervous system (e.g., central nervous system tissues) of a subject, comprising administering a composition that comprises a substantially dephosphorylated LSD protein described herein, or p97 conjugate thereof. In certain of these and related embodiments, the methods increase the rate of delivery of the agent to the central nervous system tissues, relative, for example, to delivery by a composition that comprises a relatively or normally phosphorylated LSD protein, or an unconjugated LSD protein.

In some instances, the subject has or is at risk for having a lysosomal storage disease. Certain methods thus relate to the treatment of lysosomal storage diseases in a subject in need thereof, optionally those lysosomal storage diseases associated with the central nervous system, or having CNS involvment. Exemplary lysosomal storage diseases include mucopolysaccharidosis type II (Hunter Syndrome), mucopolysaccharidosis type I (Hurler Syndrome), aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leucodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, β-mannosidosis, metachromatic leucodystrophy, mucolipidosis type I, sialidosis types I/II mucolipidosis types II/III I-cell disease, mucolipidosis type IIIC pseudo-Hurler polydystrophy, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, Morquio syndrome, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease types NB, Niemann-Pick disease, Niemann-Pick disease type C1, Niemann-Pick disease type C2, pycnodysostosis, Schindler disease types I/II, Schindler disease, and sialic acid storage disease. In these and related embodiments, the substantially dephosphorylated LSD protein can be administered alone and/or as a p97 conjugate, as described herein.

In specific aspects, the lysosomal storage disease is mucopolysaccharidosis type II (MPS II; or Hunter syndrome), and the LSD protein is a substantially dephosphorylated form of human IDS. Hunter Syndrome is an X-linked multisystem disorder characterized by glycosaminoglycans (GAG) accumulation. The vast majority of affected individuals are male; on rare occasion carrier females manifest findings. Age of onset, disease severity, and rate of progression may vary significantly.

In those with severe disease, CNS involvement (manifest primarily by progressive cognitive deterioration), progressive airway disease, and cardiac disease usually result in death in the first or second decade of life. Certain embodiments therefore include the treatment of Hunter Syndrome with CNS involvement.

In those with attenuated disease, the CNS is not (or is minimally) affected, although the effect of GAG accumulation on other organ systems may be just as severe as in those who have progressive cognitive decline. Survival into the early adult years with normal intelligence is common in the attenuated form of the disease. However, subjects with attenuated disease can still benefit from administration of dephosphorylated LSD proteins (e.g., IDS) having improved penetration into CNS tissues, for instance, to reduce the risk of progression from attenuated Hunter Syndrome to that with CNS involvement.

Additional findings in both forms of Hunter Syndrome include: short stature; macrocephaly with or without communicating hydrocephalus; macroglossia; hoarse voice; conductive and sensorineural hearing loss; hepatomegaly and/or splenomegaly; dysostosis multiplex and joint contractures including ankylosis of the temporomandibular joint; spinal stenosis; and carpal tunnel syndrome. Subjects undergoing treatment with LSD proteins described herein may thus have one or more of these findings of Hunter Syndrome.

Urine GAGs and skeletal surveys can establish the presence of an MPS condition but are not specific to MPS II. The gold standard for diagnosis of MPS II in a male proband is deficient iduronate sulfatase (IDS) enzyme activity in white cells, fibroblasts or plasma in the presence of normal activity of at least one other sulfatase. Molecular genetic testing of IDS, the only gene in which mutation is known to be associated with Hunter Syndrome, can be used to confirm the diagnosis in a male proband with an unusual phenotype or a phenotype that does not match the results of GAG testing.

Common treatments for Hunter Syndrome include developmental, occupational, and physical therapy; shunting for hydrocephalus; tonsillectomy and adenoidectomy; positive pressure ventilation (CPAP or tracheostomy); carpal tunnel release; cardiac valve replacement; inguinal hernia repair. Hence, in certain aspects, a subject for treatment by the LSD proteins described herein may be about to undergo, is undergoing, or has undergone one or more of these treatments.

Disease monitoring can depend on organ system involvement and disease severity, and usually includes annual cardiac evaluation and echocardiograms; pulmonary evaluations including pulmonary function testing; audiograms; eye examinations; developmental assessments; and neurologic examinations. Additional studies may include sleep studies for obstructive apnea; nerve conduction velocity (NCV) to assess for carpal tunnel syndrome; evaluations for hydrocephalus; orthopedic evaluations to monitor hip disease. Thus, in some aspects, a subject for treatment by the LSD proteins described herein may be about to undergo, is undergoing, or has undergone one or more of these disease monitoring protocols.

In other aspects, the LSD is mucopolysaccharidosis type I (Hurler Syndrome), and the LSD protein is a substantially dephosphorylated form of human L-iduronidase. Mucopolysaccharidosis type I (MPS I) is a progressive multisystem disorder with features ranging over a continuum of severity. While affected individuals have traditionally been classified as having one of three MPS I syndromes, Hurler syndrome, Hurler-Scheie syndrome, or Scheie syndrome, no biochemical differences have been identified and the clinical findings overlap; thus, affected individuals are most often described as having either severe or attenuated MPS I, a distinction that influences therapeutic options.

In severe MPS I, infants may appear normal at birth, and typical early manifestations are nonspecific (e.g., umbilical or inguinal hernia, frequent upper respiratory-tract infections before age 1 year). Coarsening of the facial features may not become apparent until after age one year. Gibbus deformity of the lower spine is common. Progressive skeletal dysplasia (dysostosis multiplex) involving all bones is universal. By age three years, linear growth ceases. Intellectual disability is progressive and profound. Hearing loss is common. Death, typically caused by cardiorespiratory failure, usually occurs within the first ten years of life. In certain aspects, a subject undergoing treatment with LSD proteins described herein may have severe MPS I, optionally with CNS involvement.

In attenuated MPS I, the severity and rate of disease progression range from serious life-threatening complications leading to death in the second to third decades to a normal life span complicated by significant disability from progressive joint manifestations. While some individuals have no neurologic involvement and psychomotor development may be normal in early childhood, learning disabilities can be present. Clinical onset is usually between ages three and ten years. Hearing loss and cardiac valvular disease are common. In certain aspects, a subject undergoing treatment with LSD proteins described herein may have attenuated MPS I, optionally with CNS involvement.

The diagnosis of MPS I typically relies on the demonstration of deficient activity of the lysosomal enzyme α-L-iduronidase in peripheral blood leukocytes, cultured fibroblasts, or plasma. Increased glycosaminoglycan (GAG) (e.g., heparan and dermatan sulfate) urinary excretion is also a useful preliminary test. Molecular genetic testing of IDUA, the only gene in which mutations are currently known to cause MPS I, is clinically available. Sequence analysis is expected to identify both IDUA mutations in most individuals with MPS I. Subjects undergoing treatment with LSD proteins described herein may thus have one or more of these characteristics of MPS I.

Treatment of the common manifestations of MPSI include infant learning programs/special education for developmental delays; hats with visors/sunglasses to reduce glare; cardiac valve replacement as needed; physical therapy, orthopedic surgery as needed (joint replacement, atlanto-occipital stabilization, median nerve decompression for carpal tunnel syndrome); cerebrospinal fluid (CSF) shunting for hydrocephalus; tonsillectomy and adenoidectomy for Eustachian tube dysfunction and/or upper airway obstruction; tracheostomy for sleep apnea, pulmonary hypertension, right heart failure; PE tubes; and surgical intervention for cervical myelopathy. Hence, in certain aspects, a subject for treatment by the LSD proteins described herein may be about to undergo, is undergoing, or has undergone one or more of these treatments.

Treatment or prevention of the primary manifestations of MPS I include hematopoietic stem cell transplantation (HSCT), which in selected children with severe MPS I before age two years can increase survival, reduce facial coarseness and hepatosplenomegaly, improve hearing, and maintain normal heart function. HSCT does not usually improve skeletal manifestations or corneal clouding. HSCT may slow the course of cognitive decline in children with mild, but not significant, cognitive impairment at the time of transplantation. Accordingly, in some aspects, a subject for treatment by the LSD proteins described herein may be about to undergo, is undergoing, or has undergone at least one HSCT.

Disease monitoring for MPS I can depend on a variety of factors, but may include early and continuous monitoring of head growth in infants and children; routine median nerve conduction velocity testing; and educational assessment of children with attenuated disease prior to primary school entry. Annual assessments can be performed by orthopedic surgeons, neurologists (spinal cord involvement), ophthalmologists, cardiologists (including echocardiogram), audiologists, and otolaryngologists. Thus, in some aspects, a subject for treatment by the LSD proteins described herein may be about to undergo, is undergoing, or has undergone one or more of these disease monitoring protocols.

For in vivo use, for instance, for the treatment of human disease, medical imaging, or testing, the substantially dephosphorylated LSD proteins and p97 conjugates described herein are generally incorporated into a pharmaceutical composition prior to administration. A pharmaceutical composition comprises one or more of the substantially dephosphorylated LSD proteins or p97 conjugates described herein in combination with a physiologically acceptable carrier or excipient.

To prepare a pharmaceutical composition, an effective or desired amount of one or more of the substantially dephosphorylated LSD proteins or p97 conjugates is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

Administration of the polypeptides and conjugates described herein, in pure form or in an appropriate pharmaceutical composition, can be carried out via any of the accepted modes of administration of agents for serving similar utilities. The pharmaceutical compositions can be prepared by combining a polypeptide or conjugate or conjugate-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented.

Carriers can include, for example, pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In certain embodiments, the substantially dephosphorylated LSD protein(s) and/or p97 polypeptide sequence are each, individually or as a pre-existing conjugate, bound to or encapsulated within a particle, e.g., a nanoparticle, bead, lipid formulation, lipid particle, or liposome, e.g., immunoliposome. For instance, in particular embodiments, the p97 polypeptide sequence is bound to the surface of a particle, and the substantially dephosphorylated LSD protein is bound to the surface of the particle and/or encapsulated within the particle. In some of these and related embodiments, the p97 polypeptide and the substantially dephosphorylated LSD protein(s) are covalently or operatively linked to each other only via the particle itself (e.g., nanoparticle, liposome), and are not covalently linked to each other in any other way; that is, they are bound individually to the same particle. In other embodiments, the p97 polypeptide and the substantially dephosphorylated LSD protein(s) are first covalently or non-covalently conjugated to each other, as described herein (e.g., via a linker molecule), and are then bound to or encapsulated within a particle (e.g., immunoliposome, nanoparticle). In specific embodiments, the particle is a liposome, and the composition comprises one or more p97 polypeptides, one or more substantially dephosphorylated LSD protein(s), and a mixture of lipids to form a liposome (e.g., phospholipids, mixed lipid chains with surfactant properties). In some aspects, the p97 polypeptide and the substantially dephosphorylated LSD protein(s) are individually mixed with the lipid/liposome mixture, such that the formation of liposome structures operatively links the p97 polypeptide and the substantially dephosphorylated LSD protein(s) without the need for covalent conjugation. In other aspects, the p97 polypeptide and the substantially dephosphorylated LSD protein(s) are first covalently or non-covalently conjugated to each other, as described herein, and then mixed with lipids to form a liposome. In other embodiments, the substantially dephosphorylated LSD protein(s) are bound to or encapsulated within a particle, e.g., a nanoparticle, bead, lipid formulation, lipid particle, or liposome, e.g., immunoliposome, without any p97 polypeptides. The p97 polypeptide, the substantially dephosphorylated LSD protein(s), and/or the p97-agent conjugate may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents, such as cytotoxic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described polypeptide or conjugate in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a substantially dephosphorylated LSD protein, or conjugate described herein, for treatment of a disease or condition of interest.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a substantially dephosphorylated LSD protein or conjugate as herein disclosed such that a suitable dosage will be obtained. Typically, this amount is at least 0.01% of the agent of interest in the composition. When intended for oral administration, this amount may be varied to be between 0.1 and about 70% of the weight of the composition. Certain oral pharmaceutical compositions contain between about 4% and about 75% of the agent of interest. In certain embodiments, pharmaceutical compositions and preparations according to the present invention are prepared so that a parenteral dosage unit contains between 0.01 to 10% by weight of the agent of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the conjugate or agent and thereby assists in the delivery of the compound. Suitable agents that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions comprising substantially dephosphorylated LSD proteins or conjugates as described herein may be prepared with carriers that protect the proteins against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection can be prepared by combining a composition that comprises a substantially dephosphorylated LSD protein or conjugate as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the protein(s) so as to facilitate dissolution or homogeneous suspension of the protein(s) in the aqueous delivery system.

The compositions may be administered in a therapeutically effective amount, which will vary depending upon a variety of factors including the activity of the specific compound (e.g., substantially dephosphorylated LSD protein, conjugate) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

Compositions comprising the substantially dephosphorylated LSD protein or conjugates described herein may also be administered simultaneously with, prior to, or after administration of one or more other therapeutic agents, as described herein. For instance, in one embodiment, the substantially dephosphorylated LSD protein or conjugate is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Such combination therapy may include administration of a single pharmaceutical dosage formulation which contains a compound of the invention and one or more additional active agents, as well as administration of compositions comprising conjugates of the invention and each active agent in its own separate pharmaceutical dosage formulation. For example, a conjugate as described herein and the other active agent can be administered to the patient together in a single oral dosage composition such as a tablet or capsule, or each agent administered in separate oral dosage formulations. Similarly, a conjugate as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising substantially dephosphorylated LSD proteins or conjugates and one or more additional active agents can be administered at essentially the same time, i.e., concurrently, or at separately staggered times, i.e., sequentially and in any order; combination therapy is understood to include all these regimens.

The following Examples are offered by way of illustration and not by way of limitation.

EXAMPLES

Example 1

Preparation of Dephosphorylated Iduronidase (DpIDU)

Iduronidase was treated with Affigel-immobilized potato acid phosphatase (PAP) to remove phosphate groups.

Preparation of Affigel-Immobilized PAP.

Following the protocol provided by BioRad for immobilization of proteins to Affigel, 20 ml of fresh Affigel suspension was placed in a 50 ml polypropylene screw-top tube and washed five times with MilliQ H$_2$O. Three milliliters of H$_2$O and 0.83 ml of 3M NaOAc pH 5.2 was added to a final volume of approximately 25 ml. 360 mg of PAP was solubilized in 10 ml of 0.1 M NaOAc, and 0.5 ml was retained to check the starting OD 280. The PAP solution was added to Affigel solution, mixed, and placed on rocker at 4° C. for overnight incubation.

The following morning, the gel was settled gently (e.g., 400 rpm in benchtop centrifuge for 1-2 sec., or let stand to settle gel). The supernatant was removed and retained to check the final OD 280 (to check linkage efficiency). Unlinked sites were blocked on the gel by addition of 20 ml of 1 M Tris HCl/Glycine pH 5.6, and incubation at 4° C. on a rocker for 3 hours. The blocking solution was removed from the gel and the gel was wash 4 times with 0.1 M NaOAc pH 5.2+0.01% Polysorbate 80 (Tween 80). The gel was stored at 4° C. in 0.1 M NaOAc pH 5.2+0.01% Polysorbate 80 (Tween 80) containing 0.02% Sodium Azide.

Removal of Phosphate Groups from IDU Using Immobilized PAP.

Buffer was decanted from the prepared Affigel-PAP gel. To remove sodium azide, the gel was washed four times with 15 ml of 0.1 M sodium acetate buffer pH 5.2 containing 0.01% Tween 80 (Polysorbate 80). Here, the gel was gently packed between washes by spinning in a benchtop centrifuge up to 400 rpm for 1 second.

Iduronidase used in all experiments was from PD Batch 000414 from Paul Fitzpatrick at 0.66 mg/ml by OD 280. Prior to incubation with Affigel-PAP, iduronidase was fully buffer exchanged into 0.1 M sodium acetate pH 5.2 to remove phosphates from the acidic PBS storage buffer, which would otherwise inhibit dephosphorylation. Buffer exchange for all dephosphorylation reactions was carried out by overnight dialysis of 12 ml of IDU (Pierce Slide-alyzer system, 10 K MW cutoff) at 0.66 mg/ml with 1 L of 0.1 M sodium acetate pH 5.2. Dialysis buffer was exchanged twice during the 24 hour period.

For the dephosphorylation reaction, 12 ml of iduronidase at 0.66 mg/ml in 0.1 M sodium acetate pH 5.2 and 10 ml of 0.1 M sodium acetate containing 0.01% Polysorbate 80 was added to the 15 ml volume of prepared Affigel-PAP in a 50 ml screw-top polypropylene tube. The mixture was incubated on rotary incubator at 25° C. for about 21-24 hours, and the gel was spun lightly in a benchtop centrifuge to 400 rpm for 1-2 seconds.

The supernatant containing dephosphorylated IDU was removed, the gel was washed four times with 15 ml of 0.1 M sodium acetate pH 5.2 containing 0.001% Polysorbate 80, and all supernatants were recovered. The supernatants (about 70-75 ml) were pooled and concentrated in a centricon (10 K cutoff). Buffer exchange into IDS formulation buffer (acidic PBS) was performed to achieve a final volume of about 4-5 ml. Polysorbate 80 was added to a final concentration of 0.001%. The composition was then filter sterilized with a 0.22 µM filter.

Example 2

Preparation of p97-Dephosphorylated Iduronate-2-Sulfatase (DpIDs) Conjugates

To prepare labeled test proteins and conjugates, dpIDS was prepared from recombinant IDS by treatment with acrylic bead-bound calf intestine alkaline phosphatase (CIP) to reduce the number of phosphate groups.

Recombinant IDS (4.5 ml @ 1.5 mg/ml; produced in human HT-1080 cells) was treated with pre-equilibrated CIP-Acrylic beads overnight at 37° C. with gentle mixing. CIP beads were transferred to a column, flow through (FT) was collected, and beads were washed with approximately 25 ml of PBS. All FT and wash fractions were collected and concentrated to 4.5 ml. CIP beads were then re-equilibrated with 10 mM Tris, 50 mM NaCl, 5 mM MgCl2 pH 8.0 and reused for other sub-batches of IDS. 29 mg CIP-treated dpIDS (dephosphorylated IDS) was produced in the first batch used for conjugation. No reduction of specific activity was observed for dpIDS (see Table 1). However, reduction of binding to soluble mannose-6-phosphate receptor (sM6PR) was observed, as measured by plate binding assay and by Biacore analysis (see Table 2, showing a 7-fold reduction of binding affinity of KD2, and 2-fold reduction of total response (Rmax)). Reduction of mannose-6-phospate (M6P) content was also observed, as measured by PAD-HPLC (see Table 3, showing a 17-fold or ~94-95% reduction in MP6 content).

TABLE 1

| Specific Activity | |
| --- | --- |
| Sample | Activity (U/mg) |
| IDS | 6,143 |
| CIP-Treated pool R1-R5 (dpIDS) | 6,151 |

TABLE 2

| Biacore analysis of binding to sM6PR | | | | |
| --- | --- | --- | --- | --- |
| Sample | KD1 (M) | KD2 (M) | Rmax1 (RU) | Rmax2 (RU) |
| IDS | 5.82e−8 | 8.13e−10 | 123.2 | 70.27 |
| dpIDS | 3.21e−8 | 5.94e−9 | 71.42 | 43.19 |

TABLE 3

| M6P content by PAD-HPLC | |
| --- | --- |
| Sample | pmol M6P/pmol protein |
| IDS | 2.56 |
| dpIDS | 0.15 |

For conjugation, about 28 mg (19.6 ml at 1.45 mg/ml) of dpIDS was buffer-exchanged at 6.0 ml/minute into 0.1 M potassium phosphate buffer pH 4.5 on a 2.6×33 cm Sephadex G25F column, then concentrated using two Vivaspin 20 10 kDa filters. This process yielded 16.5 ml of a dpIDS solution at 1.67 mg/ml as indicated by UV-visible spectrophotometry at 280 nm, and assuming an absorbance of 1.33 at this wavelength for a 1 mg/ml solution of dpIDS (indicated yield=28 mg). A similar protocol was performed to prepare an initial solution of IDS (normally phosphorylated), yielding 22 ml of an IDS solution at 1.45 mg/ml. These proteins were then conjugated to AlexaFluor 647 (AF647), human p97 (melanotransferrin; MTf), or both, as described below.

Incorporation of AF647 into dpIDS.

To a 11.6 mg (6.96 ml) solution of dpIDS (above) was added 2.0 mg (400 µl) of a 5.0 mg/ml solution of AlexaFluor 647 succinimide ester (Invitrogen A20006) in DMSO, equivalent to an AF647:dpIDS ratio of 10:1. The activation reaction was allowed to proceed for 35 minutes at 20° C., yielding crude AF647-labeled dpIDS. 1.08 ml of the crude reaction mix (containing 1.8 mg of dpIDS) was removed and purified into 50 mM potassium phosphate buffer+150 mM sodium chloride, pH 6.7, on a single Sephadex G25M PD-10 column. This process yielded 2.5 ml of a solution of AF647-activated dpIDS.

The solution was diafiltered using a Vivaspin 6 filter until no color was visible in the filtrate, and then concentrated to yield 1.31 ml of a dpIDS-AF647 solution with a concentration of 1.15 mg/ml, assuming an absorbance of 1.33 at this wavelength for a 1 mg/ml solution of dpIDS (yield=1.5 mg), and an AF647:IDS ratio of 2.08, assuming a molar extinction coefficient for AF647 of 239,000 L mol$^{-1}$ cm$^{-1}$ at 650 nm. This solution was filtered to 0.2 µm. This protocol was also used to incorporate AF647 into normally phosphorylated IDS.

Incorporation of Maleimides into dpIDS-AF647.

To part of the crude AF647-labeled dpIDS (9.8 mg) was added 0.23 mg (113 µl) of a 2.0 mg/ml solution of 4-[N-maleimidomethyl]cyclohexane-1-carboxylate (SMCC, Thermo 22360) in DMSO, equivalent to an SMCC:dpIDS ratio of 5:1. The dpIDS-AF647 activation reaction was allowed to proceed for 60 minutes at 20° C., then quenched for 15 minutes at 20° C. with 126 µl of a 10 mg/ml aqueous glycine solution.

The crude maleimide-activated dpIDS-AF647 was purified at 6.0 ml/minute on a 2.6×23 cm Sephadex G50M column using a 50 mM potassium phosphate, 150 mM sodium chloride, and 5 mM EDTA buffer pH 7.0 as eluent. This process yielded 14.0 ml of a solution of maleimide-activated dpIDS-AF647 with a concentration of 0.69 mg/ml assuming an absorbance of 1.33 at this wavelength for a 1 mg/ml solution of dpIDS (yield=9.71 mg), and an AF647:dpIDS ratio of 2.01, assuming a molar extinction coefficient for AF647 of 239,000 L mol$^{-1}$ cm$^{-1}$ at 650 nm. A sample was assayed for maleimide content using SAMSA-fluorescein, indicating an incorporation of 1.04 maleimide groups per dpIDS molecule. This protocol was also used to incorporate maleimides into normally phosphorylated IDS-AF647.

p97 (MTf)-dpIDS-AF647 Conjugation.

220 mg of soluble p97 (MTf) was buffer exchanged at 6.0 mg/ml on a 2.6×34 cm Sephadex G25M column into 0.1 M potassium phosphate buffer pH 7.5, then concentrated using a Vivaspin 20 10 kDa filter to yield 15.0 ml of a p97 solution at 13.91 mg/ml as indicated by UV-visible spectrophotometry at 280 nm, and assuming an absorbance of 1.19 at this wavelength for a 1 mg/ml solution of p97 (indicated yield=209 mg).

For thiolation of p97, 46 mg (3.31 ml) of p97 was thawed and equilibrated to room temperature, and 66 µl (0.33 mg) of a 5.0 mg/ml solution of S-acetylthioacetic acid and succinimidyl ester (SATA, Thermo 26102) in DMSO was added, equivalent to a SATA:p97 ratio of 2.5:1. The S-acetylthiolation reaction was allowed to proceed for 60 minutes at 20° C. An aqueous solution (0.33 ml) of 0.05 M EDTA disodium salt and 2.5 M hydroxylamine hydrochloride, pH 7.0, was added to deprotect the thiols, and the deprotection reaction was allowed to proceed for 15 minutes at 20° C.

The crude thiolated p97 was purified on two disposable PC-10 Sephadex G25M columns to remove low-molecular weight by-products, using 50 mM potassium phosphate, 150 mM sodium chloride, 5 mM EDTA buffer at pH 7.0 as an eluent. This process yielded 6.0 ml of a solution of thiolated p97 with a concentration of 7.48 mg/ml as indicated by UV-visible spectrophotometry at 280 nm, and assuming an absorbance of 1.19 at this wavelength for a 1 mg/ml solution of p97 (indicated yield=45 mg). A sample was assayed for thiol content using Ellman's Reagent, indicating an incorporation of 0.9 thiol groups per p97 molecule.

For conjugation of p97 to dpIDS-AF647, 9.2 mg of maleimide-activated dpIDS-AF647 and 17.8 mg of thiolated p97 (equivalent to a p97:dpIDS ratio of 1.8:1) were allowed to react together for 18 hours at 20° C. The conjugation reaction was quenched by the addition of 50 µl of a 2.0 mg/ml aqueous solution of 2-mercaptoethanol (incubated for 15 minutes at 20° C.) and 32 µl of a 10.0 mg/ml aqueous solution of N-ethylmaleimide (incubated for 15 minutes at 20° C.).

The crude conjugate (~16 ml) was filtered to 0.2 µm and concentrated to 4.0 ml using a Vivaspin 20 10 kDa filter. The concentrated crude conjugate was purified by high-resolution size exclusion chromatography, using a 2.6×62 cm Superdex 20PG column at 4.0 ml/min with 50 mM potassium phosphate buffer=150 mM sodium chloride (pH 6.7) as the eluent. This protocol was also used to conjugate p97 to normally phosphorylated IDS-AF647.

Example 3

Distribution of Dephosphorylated Iduronate-2-Sulfatase (DpIDS) and P97-DpIDU Conjugates in Brain Tissue Experiments were performed to evaluate distribution of AF647-labeled IDS, dpIDS, p97 (MTf)-IDS conjugates, and p97 (MTf)-dpIDS conjugates in brain tissue compartments. AlexaFluor 647 (AF647)-labeled proteins were injected intravenously into mice according to the following Table.

TABLE 4

Injected dose for dpIDS study.

| Agent | Mice | Approx. MW (g/mole) | Injected Dose (mg/kg) | Injected Dose (moles/kg) |
|---|---|---|---|---|
| IDS-AF647 | 3 | 76,000 | 6 | 7.9e−8 |
| $^{dp}$IDS-AF647 | 3 | 76,000 | 6 | 7.9e−8 |
| MTf-IDS-AF647 | 3 | 158,000 | 12.5 | 7.9e−8 |
| MTf-$^{dp}$IDS-AF647 | 3 | 158,000 | 12.5 | 7.9e−8 |

About two hours post-injection of labelled test proteins, intracardiac brain perfusion was performed to wash out blood from the cerebral vasculature without damaging the blood brain barrier. This procedure was performed prior to brain dissection and preparation of brain tissue for histological and biodistribution studies. Here, tomato lectin (100 µg) was first injected (tail vein injection) into the mice about 10 minute prior to euthanasia. The mice were anaesthetized with i.p. injection of ketamine and xylazine at a dose of 100 mg/kg and 10 mg/kg respectively. About 40 µL of 100 units/mL of heparin was then administered intraperitoneally. After the mice were unconscious, they were wetted with ethanol and the rib cage was removed to expose the beating heart. The mice were exsanguinated through the right ventricle using a 1 ml syringe fitted with 25 gauge needle. The vena cava and/or the right atrium were cut to allow for drainage of circulating perfusate. The mice were perfused through the left ventricle using a 25 gauge needle and infusion pump (4 ml/min for 2-5 min) until the liver appeared clear of blood. The scalp was split with a scalpel from between the eyes to the neck to expose the skull. The spinal cord was severed with the scalpel just below the foramen magnum. Scissors were used to cut the skull from the foramen magnum laterally towards the eyes and remove the top of the skull. Curved forceps were used to scoop out the brain without damaging the tissue.

The brain was then cut in half along the sagittal plane and each half was weighed. One half was embedded in OCT compound for freezing and the other half was prepared for homogenization and measurement of fluorescence in tissue homogenates.

Figure 2:
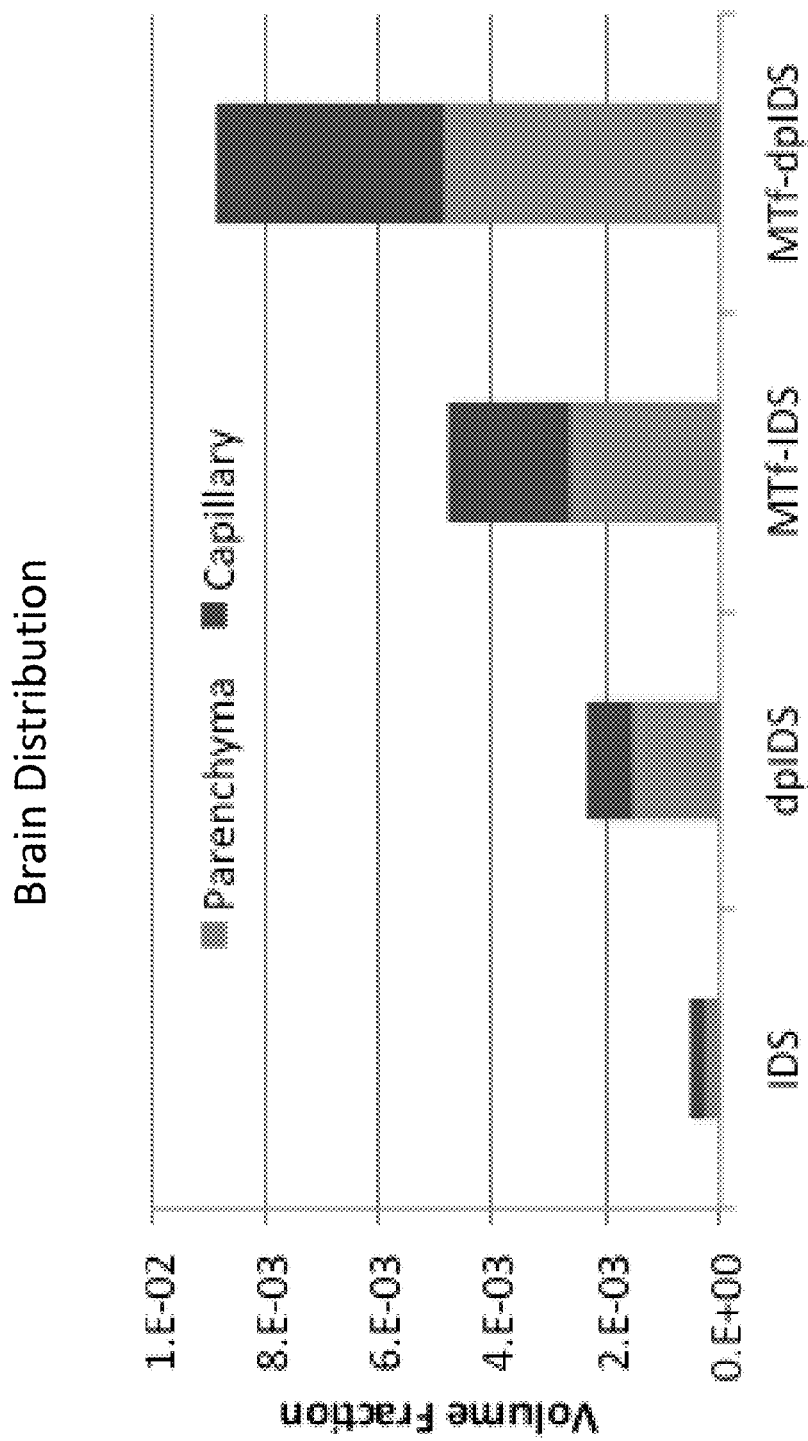
FIG. 2 shows the distribution of test proteins between brain parenchyma (inside the BBB) and brain capillaries (outside the BBB) of mice following intravenous infection.
Figure 5:
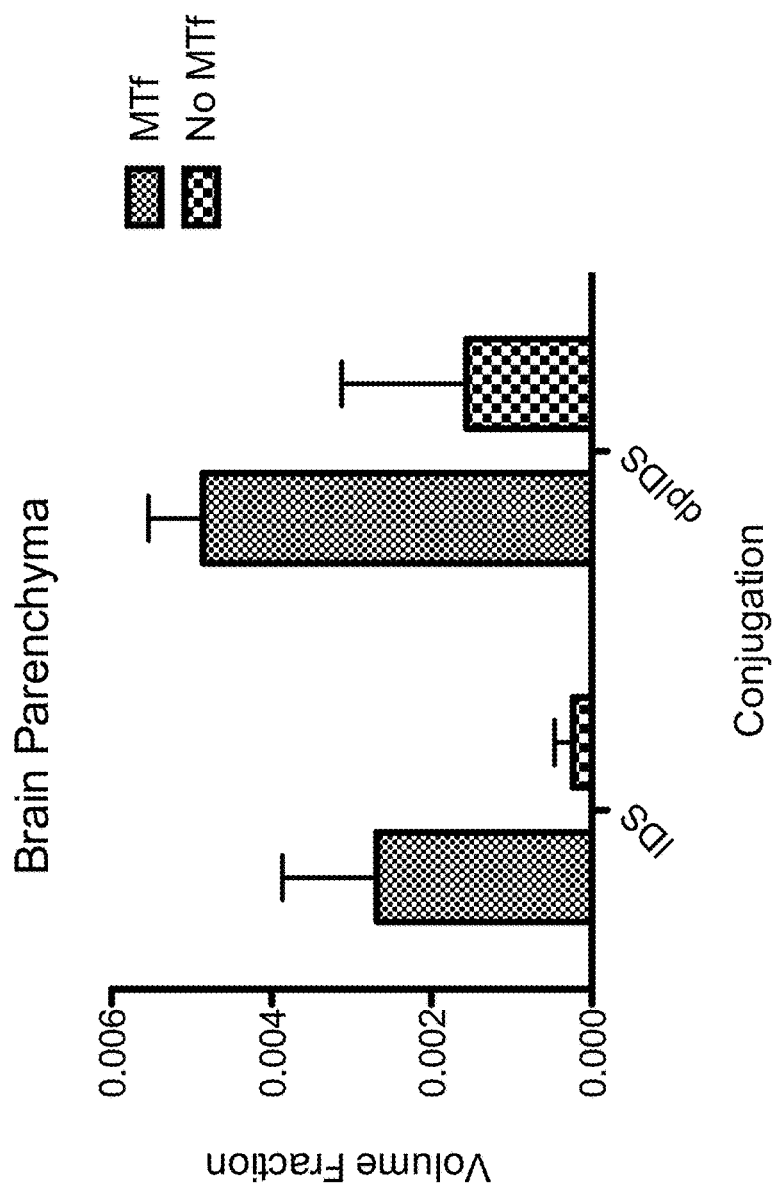
FIG. 5 shows the distribution of IDS and dpIDS in brain parenchyma, without or without conjugation to p97 (MTf).

The results are shown in FIGS. 1, 2, and 5. FIG. 1 shows the levels of test proteins accumulated in the brain parenchyma of mice following intravenous injection (IDS, iduronate-2-sulfatase; dpIDS, dephosphorylated iduronate-2-sulfatase; MTf-IDS, p97-IDS conjugate; MTf-dpIDS, p97-dpIDS conjugate). FIG. 2 shows the distribution of test proteins between brain parenchyma (inside the BBB) and brain capillaries (outside the BBB) of mice following intravenous infection. FIG. 5 shows the levels of IDS and dpIDS in the brain parenchyma, without and without conjugation to p97 (MTf).

A 2-way ANOVA analysis was also performed using these data. The results are shown in the Table below.

TABLE 5

| 2-way ANOVA. | | | |
|---|---|---|---|
| Source of Variation | Degrees of Freedom | Sum of Squares | Mean Square |
| MTf Conjugation | 1 | 8.16E−05 | 8.16E−05 |
| M6P dephosphorylation | 1 | 3.04E−05 | 3.04E−05 |
| Interaction | 1 | 1.74E−06 | 1.74E−06 |
| Residual (error) | 37 | 4.00E−05 | 1.08E−06 |
| Total | 40 | | |

Does p97 (MTf) conjugation effect the result? MTf conjugation accounts for about 53.10% of the total variance. F=75.52. DFn=1. DFd=37. The P value is <0.0001. If MTf conjugation has no effect overall, there is a less than 0.01% chance of randomly observing an effect this big (or bigger) in an experiment of this size. The effect is considered extremely significant.

Does M6P dephosphorylation effect the result? M6P dephosphorylation accounts for about 19.75% of the total variance. F=28.09. DFn=1. DFd=37. The P value is <0.0001. If M6P dephosphorylation has no effect overall, there is a less than 0.01% chance of randomly observing an effect this big (or bigger) in an experiment of this size. The effect is considered extremely significant.

According to these data and analysis, dephosphorylated IDS showed significantly increased penetration into brain parenchyma relative to normally phosphorylated IDS. Likewise, p97-dpIDS conjugates showed significantly increased penetration into brain parenchyma relative to conjugates between p97 and normally phosphorylated IDS. Hence, the removal of phosphate groups significantly increased the transfer of IDS across the BBB, whether administered alone or as a p97 conjugate.

The various embodiments described herein can be combined to provide further embodiments. All of the U.S. patents, U.S. patent application publications, U.S. patent application, foreign patents, foreign -continued Val Arg Arg Ser Ser His Val Thr Ile Asp Thr Leu Lys Gly Val Lys
            115                 120                 125

Ser Cys His Thr Gly Ile Asn Arg Thr Val Gly Trp Asn Val Pro Val
130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
            180                 185                 190

Ser Ser Gly Glu Gly Val Cys Asp Lys Ser Pro Leu Glu Arg Tyr Tyr
            195                 200                 205

Asp Tyr Ser Gly Ala Phe Arg Cys Leu Ala Glu Gly Ala Gly Asp Val
210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
            260                 265                 270

Leu Ala Arg Val Pro Ala His Ala Val Val Arg Ala Asp Thr Asp
            275                 280                 285

Gly Gly Leu Ile Phe Arg Leu Leu Asn Glu Gly Gln Arg Leu Phe Ser
290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
            340                 345                 350

Lys Gly Leu Leu Cys Asp Pro Asn Arg Leu Pro Pro Tyr Leu Arg Trp
            355                 360                 365

Cys Val Leu Ser Thr Pro Glu Ile Gln Lys Cys Gly Asp Met Ala Val
370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Thr Tyr
            420                 425                 430

Gly Leu Val Pro Ala Ala Gly Glu His Tyr Ala Pro Glu Asp Ser Ser
            435                 440                 445

Asn Ser Tyr Tyr Val Val Ala Val Val Arg Arg Asp Ser Ser His Ala
450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
            500                 505                 510

Phe Phe Asn Ala Ser Cys Val Pro Val Asn Asn Pro Lys Asn Tyr Pro
515                 520                 525

-continued

Ser Ser Leu Cys Ala Leu Cys Val Gly Asp Glu Gln Gly Arg Asn Lys
    530                 535                 540

Cys Val Gly Asn Ser Gln Glu Arg Tyr Tyr Gly Tyr Arg Gly Ala Phe
545                 550                 555                 560

Arg Cys Leu Val Glu Asn Ala Gly Asp Val Ala Phe Val Arg His Thr
                565                 570                 575

Thr Val Phe Asp Asn Thr Asn Gly His Asn Ser Glu Pro Trp Ala Ala
            580                 585                 590

Glu Leu Arg Ser Glu Asp Tyr Glu Leu Leu Cys Pro Asn Gly Ala Arg
        595                 600                 605

Ala Glu Val Ser Gln Phe Ala Ala Cys Asn Leu Ala Gln Ile Pro Pro
610                 615                 620

His Ala Val Met Val Arg Pro Asp Thr Asn Ile Phe Thr Val Tyr Gly
625                 630                 635                 640

Leu Leu Asp Lys Ala Gln Asp Leu Phe Gly Asp His Asn Lys Asn
                645                 650                 655

Gly Phe Lys Met Phe Asp Ser Ser Asn Tyr His Gly Asp Leu Leu
                660                 665                 670

Phe Lys Asp Ala Thr Val Arg Ala Val Pro Val Gly Glu Lys Thr Thr
            675                 680                 685

Tyr Arg Gly Trp Leu Gly Leu Asp Tyr Val Ala Ala Leu Glu Gly Met
690                 695                 700

Ser Ser Gln Gln Cys Ser Gly Ala Ala Ala Pro Ala Pro Gly Ala Pro
705                 710                 715                 720

Leu Leu Pro Leu Leu Leu Pro Ala Leu Ala Arg Leu Leu Pro Pro
                725                 730                 735

Ala Leu

<210> SEQ ID NO 2
<211> LENGTH: 525
<212> TYPE: PRT
<213> ORGANISM: Homo sapiens

<400> SEQUENCE: 2

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

-continued

Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
        180                 185                 190

Pro Phe Phe Leu Ala Val Gly Tyr His Lys Pro His Ile Pro Phe Arg
    195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
        260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
        340                 345                 350

Phe Pro Tyr Leu Asp Pro Phe Asp Ser Ala Ser Gln Leu Met Glu Pro
    355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
        420                 425                 430

Arg Glu Leu Ile Ala Tyr Ser Gln Tyr Pro Arg Pro Ser Asp Ile Pro
    435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
        500                 505                 510

Asp Ser Gln Gly Gly Asp Leu Phe Gln Leu Leu Met Pro
    515                 520                 525

<210> SEQ ID NO 3
<211> LENGTH: 653
<212> TYPE: PRT
<213> ORGANISM: Homo sapiens

<400> SEQUENCE: 3

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

Gln Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415
```

-continued

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
            485                 490                 495

Thr Ala Glu Gln Phe Arg Arg Met Arg Ala Ala Glu Asp Pro Val Ala
        500                 505                 510

Ala Ala Pro Arg Pro Leu Pro Ala Gly Gly Arg Leu Thr Leu Arg Pro
    515                 520                 525

Ala Leu Arg Leu Pro Ser Leu Leu Val His Val Cys Ala Arg Pro
530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
            565                 570                 575

Cys Leu Trp Thr Tyr Glu Ile Gln Phe Ser Gln Asp Gly Lys Ala Tyr
        580                 585                 590

Thr Pro Val Ser Arg Lys Pro Ser Thr Phe Asn Leu Phe Val Phe Ser
    595                 600                 605

Pro Asp Thr Gly Ala Val Ser Gly Ser Tyr Arg Val Arg Ala Leu Asp
610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
            645                 650

<210> SEQ ID NO 4
<211> LENGTH: 5
<212> TYPE: PRT
<213> ORGANISM: Artificial Sequence
<220> FEATURE:
<223> OTHER INFORMATION: Sulfatase motif
<220> FEATURE:
<221> NAME/KEY: MISC_FEATURE
<222> LOCATION: (1)..(1)
<223> OTHER INFORMATION: Xaa = Any amino acid or absent
<220> FEATURE:
<221> NAME/KEY: MISC_FEATURE
<222> LOCATION: (2)..(2)
<223> OTHER INFORMATION: Xaa = Cys or Ser
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Pro or Ala
<220> FEATURE:
<221> NAME/KEY: MISC_FEATURE
<222> LOCATION: (5)..(5)
<223> OTHER INFORMATION: Xaa = Any amino acid

<400> SEQUENCE: 4

Xaa Xaa Xaa Xaa Xaa
1               5

```
<210> SEQ ID NO 5
<211> LENGTH: 5
<212> TYPE: PRT
<213> ORGANISM: Artificial Sequence
<220> FEATURE:
<223> OTHER INFORMATION: Sulfatase motifs
<220> FEATURE:
<221> NAME/KEY: MISC_FEATURE
<222> LOCATION: (1)..(1)
<223> OTHER INFORMATION: Xaa = Any amino acid or absent
<220> FEATURE:
<221> NAME/KEY: MOD_RES
<222> LOCATION: (2)..(2)
<223> OTHER INFORMATION: Formylglycine
<220> FEATURE:
<221> NAME/KEY: MISC_FEATURE
<222> LOCATION: (3)..(3)
<223> OTHER INFORMATION: Xaa = Any amino acid or absent
<220> FEATURE:
<221> NAME/KEY: MISC_FEATURE
<222> LOCATION: (4)..(4)
<223> OTHER INFORMATION: Xaa = Pro or Ala
<220> FEATURE:
<221> NAME/KEY: MISC_FEATURE
<222> LOCATION: (5)..(5)
<223> OTHER INFORMATION: Xaa = Any amino acid

<400> SEQUENCE: 5

Xaa Gly Xaa Xaa Xaa
 1               5

<210> SEQ ID NO 6
<211> LENGTH: 4
<212> TYPE: PRT
<213> ORGANISM: Artificial Sequence
<220> FEATURE:
<223> OTHER INFORMATION: Exemplary Gly Ser linker

<400> SEQUENCE: 6

Gly Ser Gly Ser
 1

<210> SEQ ID NO 7
<211> LENGTH: 4
<212> TYPE: PRT
<213> ORGANISM: Artificial Sequence
<220> FEATURE:
<223> OTHER INFORMATION: Exemplary Gly Ser linker

<400> SEQUENCE: 7

Gly Gly Ser Gly
 1

<210> SEQ ID NO 8
<211> LENGTH: 4
<212> TYPE: PRT
<213> ORGANISM: Artificial Sequence
<220> FEATURE:
<223> OTHER INFORMATION: Exemplary Gly Ser linker

<400> SEQUENCE: 8

Gly Gly Gly Ser
 1

<210> SEQ ID NO 9
<211> LENGTH: 5
<212> TYPE: PRT
<213> ORGANISM: Artificial Sequence
<220> FEATURE:
<223> OTHER INFORMATION: Exemplary Gly Ser linker
```

```
<400> SEQUENCE: 9

Gly Gly Gly Gly Ser
1               5

<210> SEQ ID NO 10
<211> LENGTH: 4
<212> TYPE: PRT
<213> ORGANISM: Artificial Sequence
<220> FEATURE:
<223> OTHER INFORMATION: Exemplary Gly Asn linker

<400> SEQUENCE: 10

Gly Asn Gly Asn
1

<210> SEQ ID NO 11
<211> LENGTH: 4
<212> TYPE: PRT
<213> ORGANISM: Artificial Sequence
<220> FEATURE:
<223> OTHER INFORMATION: Exemplary Gly Asn linker

<400> SEQUENCE: 11

Gly Gly Asn Gly
1

<210> SEQ ID NO 12
<211> LENGTH: 4
<212> TYPE: PRT
<213> ORGANISM: Artificial Sequence
<220> FEATURE:
<223> OTHER INFORMATION: Exemplary Gly Asn linker

<400> SEQUENCE: 12

Gly Gly Gly Asn
1

<210> SEQ ID NO 13
<211> LENGTH: 5
<212> TYPE: PRT
<213> ORGANISM: Artificial Sequence
<220> FEATURE:
<223> OTHER INFORMATION: Exemplary Gly Asn linker

<400> SEQUENCE: 13

Gly Gly Gly Gly Asn
1               5

<210> SEQ ID NO 14
<211> LENGTH: 4
<212> TYPE: PRT
<213> ORGANISM: Artificial Sequence
<220> FEATURE:
<223> OTHER INFORMATION: Enzymatically degradable linker - thrombin
      cleavable

<400> SEQUENCE: 14

Gly Arg Gly Asp
1

<210> SEQ ID NO 15
<211> LENGTH: 6
<212> TYPE: PRT
<213> ORGANISM: Artificial Sequence
<220> FEATURE:
<223> OTHER INFORMATION: Enzymatically degradable linker - thrombin
      cleavable
```

```
<400> SEQUENCE: 15

Gly Arg Gly Asp Asn Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Enzymatically degradable linker - thrombin
      cleavable

<400> SEQUENCE: 16

Gly Arg Gly Asp Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Enzymatically degradable linker - thrombin
      cleavable

<400> SEQUENCE: 17

Gly Arg Gly Asp Ser Pro Lys
1               5

<210> SEQ ID NO 18
<211> LENGTH: 4
<212> TYPE: PRT
<213> ORGANISM: Artificial Sequence
<220> FEATURE:
<223> OTHER INFORMATION: Enzymatically degradable linker - elastase
      cleavable

<400> SEQUENCE: 18

Ala Ala Pro Val
1

<210> SEQ ID NO 19
<211> LENGTH: 4
<212> TYPE: PRT
<213> ORGANISM: Artificial Sequence
<220> FEATURE:
<223> OTHER INFORMATION: Enzymatically degradable linker - elastase
      cleavable

<400> SEQUENCE: 19

Ala Ala Pro Leu
1

<210> SEQ ID NO 20
<211> LENGTH: 4
<212> TYPE: PRT
<213> ORGANISM: Artificial Sequence
<220> FEATURE:
<223> OTHER INFORMATION: Enzymatically degradable linker - elastase
      cleavable

<400> SEQUENCE: 20

Ala Ala Pro Phe
1
```

```
<210> SEQ ID NO 21
<211> LENGTH: 4
<212> TYPE: PRT
<213> ORGANISM: Artificial Sequence
<220> FEATURE:
<223> OTHER INFORMATION: Enzymatically degradable linker - elastase
      cleavable

<400> SEQUENCE: 21

Ala Ala Pro Ala
1

<210> SEQ ID NO 22
<211> LENGTH: 4
<212> TYPE: PRT
<213> ORGANISM: Artificial Sequence
<220> FEATURE:
<223> OTHER INFORMATION: Enzymatically degradable linker - elastase
      cleavable

<400> SEQUENCE: 22

Ala Tyr Leu Val
1

<210> SEQ ID NO 23
<211> LENGTH: 6
<212> TYPE: PRT
<213> ORGANISM: Artificial Sequence
<220> FEATURE:
<223> OTHER INFORMATION: Enzymatically degradable linker - matrix
      metalloproteinase cleavable
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (6)..(6)
<223> OTHER INFORMATION: Xaa = Any amino acid

<400> SEQUENCE: 23

Gly Pro Xaa Gly Pro Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: Enzymatically degradable linker - matrix
      metalloproteinase cleavable
<220> FEATURE:
<221> NAME/KEY: MISC_FEATURE
<222> LOCATION: (6)..(6)
<223> OTHER INFORMATION: Xaa = Any amino acid

<400> SEQUENCE: 24

Gly Pro Leu Gly Pro Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Enzymatically degradable linker - matrix
      metalloproteinase cleavable
<220> FEATURE:
<221> NAME/KEY: MISC_FEATURE
<222> LOCATION: (6)..(6)
<223> OTHER INFORMATION: Xaa = Any amino acid
```

```
<400> SEQUENCE: 25

Gly Pro Ile Gly Pro Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Enzymatically degradable linker - matrix
      metalloproteinase cleavable
<220> FEATURE:
<221> NAME/KEY: MISC_FEATURE
<222> LOCATION: (5)..(5)
<223> OTHER INFORMATION: Xaa = Any amino acid

<400> SEQUENCE: 26

Ala Pro Gly Leu Xaa
1               5

<210> SEQ ID NO 27
<211> LENGTH: 7
<212> TYPE: PRT
<213> ORGANISM: Artificial Sequence
<220> FEATURE:
<223> OTHER INFORMATION: Enzymatically degradable linker - collagenase
      cleavable
<220> FEATURE:
<221> NAME/KEY: MISC_FEATURE
<222> LOCATION: (7)..(7)
<223> OTHER INFORMATION: Xaa = Any amino acid

<400> SEQUENCE: 27

Pro Leu Gly Pro Asp Arg Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Enzymatically degradable linker - collagenase
      cleavable
<220> FEATURE:
<221> NAME/KEY: MISC_FEATURE
<222> LOCATION: (7)..(7)
<223> OTHER INFORMATION: Xaa = Any amino acid

<400> SEQUENCE: 28

Pro Leu Gly Leu Leu Gly Xaa
1               5

<210> SEQ ID NO 29
<211> LENGTH: 7
<212> TYPE: PRT
<213> ORGANISM: Artificial Sequence
<220> FEATURE:
<223> OTHER INFORMATION: Enzymatically degradable linker - collagenase
      cleavable

<400> SEQUENCE: 29

Pro Gln Gly Ile Ala Gly Trp
1               5

<210> SEQ ID NO 30
<211> LENGTH: 5
<212> TYPE: PRT
<213> ORGANISM: Artificial Sequence
```

```
<220> FEATURE:
<223> OTHER INFORMATION: Enzymatically degradable linker - collagenase
      cleavable

<400> SEQUENCE: 30

Pro Leu Gly Cys His
1               5

<210> SEQ ID NO 31
<211> LENGTH: 6
<212> TYPE: PRT
<213> ORGANISM: Artificial Sequence
<220> FEATURE:
<223> OTHER INFORMATION: Enzymatically degradable linker - collagenase
      cleavable

<400> SEQUENCE: 31

Pro Leu Gly Leu Tyr Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Enzymatically degradable linker - collagenase
      cleavable

<400> SEQUENCE: 32

Pro Leu Ala Leu Trp Ala Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Enzymatically degradable linker - collagenase
      cleavable

<400> SEQUENCE: 33

Pro Leu Ala Tyr Trp Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Enzymatically degradable linker - stromelysin
      cleavable

<400> SEQUENCE: 34

Pro Tyr Ala Tyr Tyr Met Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Enzymatically degradable linker - gelatinase
      cleavable

<400> SEQUENCE: 35

Pro Leu Gly Met Tyr Ser Arg
1               5
```

```
<210> SEQ ID NO 36
<211> LENGTH: 4
<212> TYPE: PRT
<213> ORGANISM: Artificial Sequence
<220> FEATURE:
<223> OTHER INFORMATION: Enzymatically degradable linker - angiotensin
      converting enzyme cleavable

<400> SEQUENCE: 36

Gly Asp Lys Pro
1

<210> SEQ ID NO 37
<211> LENGTH: 5
<212> TYPE: PRT
<213> ORGANISM: Artificial Sequence
<220> FEATURE:
<223> OTHER INFORMATION: Enzymatically degradable linker - angiotensin
      converting enzyme cleavable

<400> SEQUENCE: 37

Gly Ser Asp Lys Pro
1               5

<210> SEQ ID NO 38
<211> LENGTH: 4
<212> TYPE: PRT
<213> ORGANISM: Artificial Sequence
<220> FEATURE:
<223> OTHER INFORMATION: Enzymatically degradable linker - cathepsin B
      cleavable

<400> SEQUENCE: 38

Ala Leu Ala Leu
1

<210> SEQ ID NO 39
<211> LENGTH: 4
<212> TYPE: PRT
<213> ORGANISM: Artificial Sequence
<220> FEATURE:
<223> OTHER INFORMATION: Enzymatically degradable linker - cathepsin B
      cleavable

<400> SEQUENCE: 39

Gly Phe Leu Gly
1
```

The invention claimed is:

1. A conjugate, comprising a p97 polypeptide that is covalently or operatively linked to a recombinant human iduronate-2-sulfatase (IDS) polypeptide that is at least 90% identical to SEQ ID NO:2, where the mannose-6-phosphate (M6P) content of the IDS polypeptide is less than 1.2 pmol M6P/pmol IDS polypeptide and wherein the IDS polypeptide has oligomannose glycans at all 8 of the N-linked glycosylation sites to form a p97 conjugate.

2. A composition, comprising the conjugate of claim 1, and a pharmaceutically acceptable carrier, where the conjugate is at least 80% pure.

3. The composition of claim 2, where the human IDS polypeptide is dephosphorylated by enzymatic digestion with an acid phosphatase or an alkaline phosphatase.

4. The composition of claim 3, where the IDS polypeptide has a M6P content of less than 0.5 pmol M6P/pmol IDS polypeptide, or about 0.15 pmol M6P/pmol IDS polypeptide.

5. The composition of claim 2, where the human IDS polypeptide is at least 95% identical to SEQ ID NO:2.

6. The composition of claim 5, where the M6P content is less than 0.5 pmol M6P/pmol IDS polypeptide.

7. The composition of claim 5, where the M6P content is about or less than 0.15 pmol M6P/pmol IDS polypeptide.

* * * * *